(12) United States Patent
Husain et al.

(10) Patent No.: US 10,959,670 B2
(45) Date of Patent: Mar. 30, 2021

(54) AUTOMATED, OBJECTIVE METHOD OF ASSESSING TINNITUS CONDITION

(71) Applicant: THE BOARD OF TRUSTEES OF THE UNIVERSITY OF ILLINOIS, Urbana, IL (US)

(72) Inventors: Fatima T. Husain, Champaign, IL (US); Yuliy Baryshnikov, Urbana, IL (US); Benjamin Joseph Zimmerman, Urbana, IL (US); Ivan Thomas Abraham, Urbana, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 44 days.

(21) Appl. No.: 16/196,587

(22) Filed: Nov. 20, 2018

(65) Prior Publication Data

US 2019/0223786 A1 Jul. 25, 2019

Related U.S. Application Data

(60) Provisional application No. 62/588,730, filed on Nov. 20, 2017.

(51) Int. Cl.
*A61B 5/00* (2006.01)
*G01R 33/56* (2006.01)
(Continued)

(52) U.S. Cl.
CPC ............ *A61B 5/4848* (2013.01); *A61B 5/128* (2013.01); *G01R 33/4806* (2013.01); *G01R 33/5608* (2013.01)

(58) Field of Classification Search
CPC .. A61B 5/4848; A61B 5/128; G01R 33/4806; G01R 33/5608
See application file for complete search history.

(56) References Cited

U.S. PATENT DOCUMENTS

| | | | |
|---|---|---|---|
| 2006/0036297 A1* | 2/2006 | Seidman | ............... A61N 1/361 607/55 |
| 2008/0001600 A1* | 1/2008 | deCharms | .......... G01R 33/4806 324/309 |

(Continued)

OTHER PUBLICATIONS

Abnormal Baseline Brain Activity in Patients with Pulsatile Tinnitus: A Resting-State fMRI Study; Hindawi Publishing Corporation, Neural Plasticity, vol. 2014, Article ID 549162, Pub. Apr. 24, 2014 (Year: 2014).*

(Continued)

*Primary Examiner* — Akm Zakaria
(74) *Attorney, Agent, or Firm* — Leydig, Voit & Mayer, Ltd.

(57) ABSTRACT

Described herein are systems and methods for determining or quantifying tinnitus conditions within a patient, including determining if a patient has some form of tinnitus as well as categorizing or determining the severity of a tinnitus condition, if present. The described systems and methods are also useful in evaluating the efficacy a tinnitus treatment by measuring the degree of reduction of tinnitus symptoms in a patient. The described systems and methods also provide a personalized profile for each specific patient, allowing for more effective treatment options as various forms or causes of tinnitus become apparent.

23 Claims, 21 Drawing Sheets

Figure 1B:
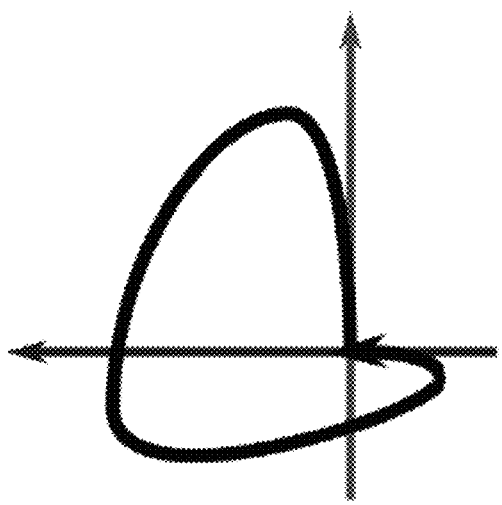

(51) Int. Cl.
  *G01R 33/48* (2006.01)
  *A61B 5/12* (2006.01)

(56) References Cited

U.S. PATENT DOCUMENTS

| | | | | |
|---|---|---|---|---|
| 2011/0044524 | A1* | 2/2011 | Wang | G01R 33/54 |
| | | | | 382/131 |
| 2014/0275960 | A1* | 9/2014 | Hubbard | A61B 5/055 |
| | | | | 600/410 |
| 2016/0209487 | A1* | 7/2016 | Stern | G01R 33/4806 |
| 2016/0225146 | A1* | 8/2016 | Frank | A61B 5/0042 |
| 2017/0128025 | A1* | 5/2017 | Chen | A61B 5/7203 |

OTHER PUBLICATIONS

Altered Regional and Circuit Resting-State Activity Associated with Unilateral Hearing Loss; PLoS One 9(5): e96126. doi:10.1371/journal.pone.0096126; Pub. May 1, 2014 (Year: 2014).*
Adjamian et al. (2009) "The mechanisms of tinnitus: Perspectives from human functional neuroimaging," Hearing Research 253(1-2): 15-31.
Agosta et al. (2012) "Resting state fMRI in Alzheimer's disease: beyond the default mode network," Neurobiology of aging 33: 1564-1578.
Allan et al. (Sep. 2016) "Neuroanatomical alterations in tinnitus assessed with magnetic resonance imaging," Frontiers in Aging Neuroscience 8: 1-14.
Anderson et al. (2011) "Reproducibility of single-subject functional connectivity measurements," AJNR Am J Neuroradiol 32: 548-555.
Ballabio et al. (2013) "Classification tools in chemistry. Part 1: Linear models. PLS-DA," Analytical Methods 5(16): 3790-3798.
Barkhof et al. (2014) "Resting-state functional MR imaging: A new window to the brain," Radiology 272(1): 29-49.
Baryshnikov et al. (Dec. 2016) "Cyclicity in multivariate time series and applications to functional MRI data," In 2016 IEEE 55th conference on decision and control (CDC): 1625-1630.
Beck et al. (1984) "Internal consistencies of the original and revised Beck Depression Inventory," J Clin Psychol 40:1365-1367.
Birn et al. (2013) "The effect of scan length on the reliability of resting-state fMRI connectivity estimates," Neuroimage 83:550-558, 20 pp.
Bressler et al. (2010) "Large-scale brain networks in cognition: emerging methods and principles," Trends in cognitive sciences 14(6): 277-290.
Brett et al. (2002) "Region of interest analysis using an SPM toolbox," In: 8th International Conference of the Organization of Human Brain Mapping, vol. 16 Sendai, Japan, 1 pp.
Brett et al. (2002) "Region of interest analysis using the marsbar toolbox for spm 99," Neuro-Image 16(2): S497 (1 pp.).
Burton et al. (2012) "Altered networks in bothersome tinnitus: A functional connectivity study," BMC Neuroscience 13(1): 1-15.
Carpenter-Thompson et al. (2014) "Alterations of the emotional processing system may underlie preserved rapid reaction time in tinnitus," Brain Res 1567:28-41.
Carpenter-Thompson et al. (2015) "Increased frontal response may underlie decreased tinnitus severity," PLoS One 10(12): 1-23.
Chen et al. (1958) "Integration of paths—A faithful representation of paths by noncommutative formal power series," Transactions of the American Mathematical Society 89(2): 395-407.
Chen et al. (1971) "Algebras of iterated path integrals and fundamental groups," Transactions of the American Mathematical Society 156: 359-379.
Chen et al. (2011) "Classification of Alzheimer disease, mild cognitive impairment, and normal cognitive status with large-scale network analysis based on resting-state functional MR imaging," Radiology 259(1):213-221.
Chen et al. (2013) "Inferring group-wise consistent multimodal brain networks via multi-view spectral clustering," IEEE Transactions on Medical Imaging 32(9): 1576-1586.

Chevyrev et al. (Mar. 2016) "A primer on the signature method in machine learning," arXiv, [stat.ML] Retrieved from http://arxiv.org/abs/1603.03788: 47 pp.
Coelho et al. (2013) "Zinc to treat tinnitus in the elderly: a randomized placebo controlled crossover trial," Otol Neurotol 34:1146-1154.
Davies et al. (2014) "Auditory network connectivity in tinnitus patients: a resting-state fMRI study," Int J Audiol 53(3):192-198.
Davies et al. (Feb. 2017) "Does chronic tinnitus alter the emotional response function of the amygdala?: A sound-evoked fMRI study," Frontiers in Aging Neuroscience 9: 1-12.
Delb et al. (2008) "Alterations in Event Related Potentials (ERP) associated with tinnitus distress and attention," Appl Psychophysiol Biofeedback 33:211-221.
Dodziuk (1976) "Finite-difference approach to the hodge theory of harmonic forms," American Journal of Mathematics 98(1): 79-104.
Dosi et al. (2006) "An evolutionary model of endogenous business cycles," Computational Economics 27(1): 3-34.
Duplantier (1989) "Areas of planar brownian curves," Journal of Physics A: Mathematical and General 22(15): 3033-3048.
Eigen et al. (1977) "A principle of natural self-organization," Naturwissenschaften 64(11): 541-565.
Faul et al. (2007) "G*Power 3: a flexible statistical power analysis program for the social, behavioral, and biomedical sciences," Behav Res Methods 39(2):175-191.
Faul et al. (2009) "Statistical power analyses using G*Power 3.1: tests for correlation and regression analyses," Behav Res Methods 41(4):1149-1160.
Folstein et al. (1975) "'Mini-mental state'. A practical method for grading the cognitive state of patients for the clinician," J Psychiatr Res 12:189-198.
Fox et al. (2005) "The human brain is intrinsically organized into dynamic, anticorrelated functional networks," Proceedings of the National Academy of Sciences of the United States of America 102(27): 9673-9678.
Fox et al. (2007) "Spontaneous fluctuations in brain activity observed with functional magnetic resonance imaging," Nature Reviews Neuroscience 8(9): 700-711.
Franco et al. (2013) "Impact of analysis methods on the reproducibility and reliability of resting-state networks," Brain connectivity 3(4):363-374.
Friston et al. (1999) "How many subjects constitute a study?," NeuroImage 10(1): 1-5.
Friston (2011) "Functional and effective connectivity: a review," Brain connectivity 1(1): 13-36.
Greicius et al. (2004) "Default-mode network activity distinguishes Alzheimer's disease from healthy aging: evidence from functional MRI," Proc Natl Acad Sci USA 101(13):4637-4642.
Greicius (2008) "Resting-state functional connectivity in neuropsychiatric disorders," Curr Opin Neurol 21:424-430.
Hassan et al. (2014) "EEG source connectivity analysis: from dense array recordings to brain networks," PLoS One 9(8):e105041, pp. 1-15.
Husain (2013) "Effect of tinnitus on distortion product otoacoustic emissions varies with hearing loss," Am J Audiol 22:125-134.
Husain et al. (2014) "Using resting state functional connectivity to unravel networks of tinnitus," Hearing Research 307: 153-162.
Husain (Apr. 2016) "Neural networks of tinnitus in humans: Elucidating severity and habituation," Hearing Research 334: 37-48.
Hutchinson et al. (2013) "Dynamic functional connectivity: promise, issues, and interpretations," Neuroimage 80: 360-378.
Jain (2010) "Data clustering: 50 years beyond K-means," Pattern Recogn Lett 31:651-666.
Keilholz (2014) "The neural basis of time-varying resting-state functional connectivity," Brain Connectivity 4(10): 769-779.
Kim et al. (2012) "Alteration of functional connectivity in tinnitus brain revealed by resting-state fMRI? A pilot study," Int J Audiol 51(5):413-417.
Koch et al. (2012) "Diagnostic power of default mode network resting state fMRI in the detection of Alzheimer's disease," Neurobiology of aging 33:466-478.
Leaver et al. (2012) "Cortico-limbic morphology separates tinnitus from tinnitus distress," Front Syst Neurosci 6:21, pp. 1-14.

(56) References Cited

OTHER PUBLICATIONS

Lockwood et al. (1998) "The functional neuroanatomy of tinnitus: evidence for limbic system links and neural plasticity," Neurology 50:114-120.
Lum et al. (2013) "Extracting insights from the shape of complex data using topology," Scientific reports 3:1236, pp. 1-8.
Mannfolk et al. (2011) "Can resting-state functional MRI serve as a complement to task-based mapping of sensorimotor function? A test-retest reliability study in healthy volunteers," Journal of Magnetic Resonance Imaging 34(3): 511-517.
Mantini et al. (2007) "Electrophysiological signatures of resting state networks in the human brain," Proceedings of the National Academy of Sciences of the United States of America 104(32): 13170-13175.
Maudoux et al. (2012) "Auditory resting-state network connectivity in tinnitus: A functional MRI study," PLoS One 7(5): 1-9.
Maudoux et al.(2012) "Connectivity graph analysis of the auditory resting state network in tinnitus," Brain Research 1485: 10-21.
Meikle et al. (2012) "The Tinnitus Functional Index: Development of a New Clinical Measure for Chronic, Intrusive Tinnitus," Ear & Hearing 33(2): 153-176.
Melcher et al. (2009) "The auditory midbrain of people with tinnitus: abnormal sound-evoked activity revisited," Hear Res 257:63-74.
Mitra et al. (2015) "Lag threads organize the brain's intrinsic activity" and "Correction" (pp. E7307), Proceedings of the National Academy of Sciences of the United States of America 112(17): E2235-E2244.
Møller (2007) "Tinnitus: Presence and future," Progress in Brain Research 166: 3-16.
Mühlnickel et al. (1998) "Reorganization of auditory cortex in tinnitus," Proc Natl Acad Sci USA 95:10340-10343.
Mumford et al. (2008) "Power calculation for group fMRI studies accounting for arbitrary design and temporal autocorrelation," Neuroimage 39:261-268.
Mumford (2012) "A power calculation guide for fMRI studies," Soc Cogn Affect Neurosci 7:738-742.
Newman et al. (1996) "Development of the Tinnitus Handicap Inventory," Arch Otolaryngol Head Neck Surg 122:143-148.
Pan et al. (2009) "The relationship between tinnitus pitch and the audiogram," Int J Audiol 48(5):277-294.
Raichle et al. (2007) "A default mode of brain function: A brief history of an evolving idea," NeuroImage 37(4): 1083-1090.
Ranaweera et al. (publicly available Oct. 2015) "Temporal pattern of acoustic imaging noise asymmetrically modulates activation in the auditory cortex," Hearing research 331: 57-68 (published Jan. 2016).
Rand (1971) "Objective Criteria for Evaluation of Clustering Methods," J Am Stat Assoc 66:846-850.
Rauschecker et al. (2010) "Tuning out the noise: limbic-auditory interactions in tinnitus," Neuron 66:819-826.
Roberts et al. (2013) "Role of attention in the generation and modulation of tinnitus," Neurosci Biobehav Rev 37:1754-1773.
Rousseeuw (1987) "Silhouettes: A graphical aid to the interpretation and validation of cluster analysis," Journal of Computational and Applied Mathematics 20:53-65.
Schmidt et al. (2013) "Default mode, dorsal attention and auditory resting state networks exhibit differential functional connectivity in tinnitus and hearing loss," PLoS One 8(10): 1-12.
Schmidt et al. (available online Jul. 2017) "Connectivity of precuneus to the default mode and dorsal attention network: A possible invariant marker of long-term tinnitus," NeuroImage: Clinical 16: 196-204.
Shehzad et al. (2009) "The resting brain: Unconstrained yet reliable," Cerebral Cortex 19(10): 2209-2229.
Sheline et al. (2001) "Increased amygdala response to masked emotional faces in depressed subjects resolves with antidepressant treatment: An fMRI study," Biological Psychiatry 50(9): 651-658.
Shi et al. (2000) "Normalized cuts and image segmentation," IEEE transactions on pattern analysis and machine intelligence 22(8):888-905.
Shore (2011) "Plasticity of somatosensory inputs to the cochlear nucleus—implications for tinnitus," Hear Res 281:38-46.
Shulman et al. (1997) "Common blood flow changes across visual tasks: II. Decreases in cerebral cortex," Journal of Cognitive Neuroscience 9(5): 648-663.
Simonetti et al. (2015) "Tinnitus neural mechanisms and structural changes in the brain: The contribution of neuroimaging research," International Archives of Otorhinolaryngology 19(3): 259-265.
Smits et al. (2007) "Lateralization of functional magnetic resonance imaging (fMRI) activation in the auditory pathway of patients with lateralized tinnitus," Neuroradiology 49:669-679.
Steer et al. (1998) "Common and specific dimensions of self-reported anxiety and depression: the BDI-II versus the BDI-IA," Behav Res Ther 37:183-190.
Stouffer et al. (1990) "Characterization of tinnitus by tinnitus patients," J Speech Hear Disord 55:439-453.
Trevis et al. (Aug. 2016) "Cognitive mechanisms in chronic tinnitus: Psychological markers of a failure to switch attention," Frontiers in Psychology 7: 1-12.
Turchin et al. (2000) "Are lemmings prey or predators?," Nature 405(6786): 562-565.
Tyler et al. (1983) "The determination of tinnitus loudness considering the effects of recruitment," J Speech Hear Res 26:59-72.
Tyler et al. (2008) "Identifying tinnitus subgroups with cluster analysis," Am J Audiol 17:S176-S184.
Tyler et al. (2014) "Development and validation of the tinnitus primary function questionnaire," Am J Audiol 23:260-272.
Ueyama et al. (2013) "Brain regions responsible for tinnitus distress and loudness: a resting-state FMRI study," PLoS One 8(6):e67778, pp. 1-12.
Van Den Heuvel et al. (2010) "Exploring the brain network: a review on resting-state fmri functional connectivity," European Neuropsychopharmacology 20(8): 519-534.
Vanneste et al. (2011) "Do tDCS and TMS influence tinnitus transiently via a direct cortical and indirect somatosensory modulating effect? A combined TMS-tDCS and TENS study," Brain Stimul 4:242-252.
Van 'T Veer et al. (2002) "Gene expression profiling predicts clinical outcome of breast cancer," Nature 415:530-536.
Veer et al. (2010) "Whole brain resting-state analysis reveals decreased functional connectivity in major depression," Frontiers in Systems Neuroscience 4: 1-10.
Ware et al. (1998) "Overview of the SF-36 Health Survey and the International Quality of Life Assessment (IQOLA) Project," Journal of clinical epidemiology 51(11):903-912.
Whitfield-Gabrieli et al. (2012) "Conn: A functional connectivity toolbox for correlated and anticorrelated brain networks," Brain Connectivity 2(3): 125-141.
Wineland et al. (2012) "Functional connectivity networks in nonbothersome tinnitus," Otolaryngology—Head and Neck Surgery 147(5): 900-906.
Zimmerman et al. (publicly available Oct. 2018) "Dissociating tinnitus patients from healthy controls using resting-state cyclicity analysis and clustering," Network Neuroscience (2019), 3(1): 67-89.

* cited by examiner

AUTOMATED, OBJECTIVE METHOD OF ASSESSING TINNITUS CONDITION

CROSS-REFERENCE TO RELATED APPLICATIONS

This patent application claims priority to and the benefit of U.S. Provisional Patent Application No. 62/588,730 filed Nov. 20, 2017 which is incorporated by reference in its entirety.

STATEMENT REGARDING FEDERALLY SPONSORED RESEARCH OR DEVELOPMENT

This invention was made with government support under W81XWH-15-2-0032 awarded by the U.S. Department of Defense. The government has certain rights in the invention.

BACKGROUND OF THE INVENTION

Subjective tinnitus is an auditory illusion that is not associated with any physical sound. According to the VA National Center for Rehabilitative Auditory Research, about 3-4 million veterans are affected by tinnitus (www.ncrar.org). Tinnitus is the most prevalent service-connected disability for all Veterans, as well as among war Veterans specifically returning from Iraq and Afghanistan. It has been estimated that the Veterans Benefits Administration pays more than $1.2 billion per year in compensation for hearing loss and tinnitus (Veterans Health Administration, 2009). At present there is no cure for tinnitus, although there are therapies that alleviate the distress associate with it for some portion of the population. One major obstacle in finding a cure is that there are likely many different types of tinnitus, and potential cures will likely have to be individually focused on these subtypes.

Some progress has been made in understanding mechanisms of tinnitus using several techniques ranging from animal physiological studies to brain imaging studies, but questions remain. In particular, there is a poor understanding of how neural mechanisms of tinnitus relate to behavioral measures of severity and to the heterogeneity of the tinnitus population. The heterogeneity of the tinnitus population has several driving factors. These include the type of sound perceived (tone, buzzing, crickets, etc.); the location of the sound relative to the head (left, right, center); the severity of accompanying hearing loss, a condition highly comorbid with tinnitus; and the age at which onset of the percept occurred. This onset can be driven by many pathologies, including sudden sensorineural hearing loss, presbycusis, acoustic neurinomas, ototoxicity, chronic noise trauma, acute acoustic trauma, and Meniere's disease (Spoendlin, 1987, Tyler, 2000). However, in some cases of tinnitus there is no accompanying hearing loss or pathology (Barnea et al., 1990).

One major variable among the tinnitus population is their reaction to the chronic sound. This reaction ranges from mild to severe, with the latter reaction type having a major impact on a person's life, making sleep difficult and making intellectual work challenging, and it may lead to depression or anxiety (Davis and Rafaie, 2000). Subgroups within the tinnitus population, in particular those associated with tinnitus severity, may have different neural underpinnings. This may relate to why certain tinnitus therapies are successful in some tinnitus patients and not in others. The present disclosure is concerned with an individual's emotional reaction to the tinnitus sound, which will be gauged by tinnitus severity/handicap questionnaires. The subgroups we will examine in our study will relate to variations in tinnitus severity.

In the past few decades, with advances in brain imaging, studies have begun to focus on diverse neural networks that may subserve the generation of tinnitus and an individual's reaction to it. The primary focus has been on the auditory pathways (e.g., Muhlnickel et al., 1998, Andersson et al., 2000, Smits et al., 2007, Melcher et al., 2009). Additionally, the abnormal involvement of non-classical auditory pathways, which receive input from the emotion-processing (Lockwood et al., 1998, Rauschecker et al., 2010, Leaver et al., 2012, Carpenter-Thompson et al., 2014), attention-processing (Delb et al., 2008, Roberts et al., 2013, Schmidt et al., 2013), somatosensory (Shore, 2011, Vanneste et al., 2011) and visual (Burton et al., 2012) pathways, may modulate tinnitus. Critical to treating and managing tinnitus is a better understanding of its neural mechanisms and the determination of its objective biomarkers, which might have prognostic and therapeutic use. Described herein is the use of resting state functional magnetic resonance imaging (fMRI), wherein participants do not perform any task and spontaneous fluctuations in brain activity are measured, to investigate these biomarkers.

It can be seen from the foregoing that there remains a need in the art for systems and methods for identification and treatments of tinnitus conditions, including diagnosis, categorization, classification, treatment and measurement of treatment efficacy in order to provide medical professional the necessary tools to help patients afflicted with tinnitus.

BRIEF SUMMARY OF THE INVENTION

Described herein are systems and methods for determining or quantifying tinnitus conditions within a patient, including determining if a patient has some form of tinnitus as well as categorizing or determining the severity of a tinnitus condition if present. The described systems and methods are also useful in evaluating the efficacy a tinnitus treatment by measuring the degree of reduction of tinnitus symptoms in a patient. The described systems and methods also provide a personalized profile for each specific patient, allowing for more effective treatment options as various forms or causes of tinnitus become apparent.

The described systems and methods couple use of functional magnetic resonance imaging (fMRI) with advanced processing and analysis to measure and identify brain activity that is associated with tinnitus. Further, in some cases, patients are evaluated in a resting state where stimuli (either external or internal) is reduced in order to more effectively identify the specific brain activity that corresponds to tinnitus.

In an aspect, provided is a method for determining a tinnitus condition of a patient comprising: i) providing a functional magnetic resonance imaging (fMRI) device; ii) imaging said patient with said fMRI thereby generating a fMRI map of at least a portion of a brain said patient; ii) identifying a plurality of voxels in said fMRI map corresponding to regions of said brain of said patient; iii) analyzing said plurality of voxels, thereby determining a tinnitus condition of said patient.

A tinnitus condition may be: the presence of or absence of tinnitus in the patient; a stage of progression of tinnitus in said patient; a type or severity of tinnitus of said patient, and/or a measure of efficacy of a tinnitus treatment.

The plurality of voxels may comprise one or more voxels corresponding to the amygdala region of said brain of said patient. The plurality of voxels may comprise one or more voxels corresponding to the precuneus region of said brain of said patient. The plurality of voxels may comprise one or more voxels corresponding to the amygdala region and the precuneus region of said brain of said patient.

The one or more functional connections may include at least one functional connection between voxels corresponding to said amygdala region and said precuneus region of said brain of said patient. The step of identifying a plurality of voxels may identify a number of voxels selected from the range of 1 to 100 voxels, 5 to 40 voxels, 10 to 40 voxels, or optionally, 15 to 35 voxels. The step of identifying a plurality of voxels may identify a number of voxels greater than or equal to 10 voxels, 15 voxels, 30 voxels, 50 voxels, or optionally, 100 voxels.

The step of imaging said patient with said fMRI may be performed over a predetermined period of time and wherein each of said plurality of voxels includes a time component. The step of analyzing said plurality of voxels may include analyzing said plurality of voxels in the time domain. The step of analyzing said plurality of voxels may further comprise invariant analysis with respect to reparamertrization of activity in said voxels with respect to time. The step of performing said fMRI may generate said fMRI map as a time series of blood oxygen levels corresponding to a time period of greater than or equal to 2 minutes, greater than or equal to 5 minutes, greater than or equal to 10 minutes, or optionally, greater than or equal to 30 minutes.

The step of analyzing said plurality of voxels may include iteratively integrating at least a portion of a time series corresponding to each of said plurality of voxels thereby generating a plurality of irreducible trajectories. The step of analyzing said plurality of voxels may further comprise generating a lead matrix comprised of a plurality of signed areas wherein determination of the sign is informed by the direction of traversal of said irreducible trajectories.

The step of analyzing said plurality of voxels may utilize the chain of offsets model. The step of analyzing said plurality of voxels further comprise a step of reducing noise in said fMRI map. The step of analyzing said plurality of voxels may further comprise comparing said plurality of voxels to a library of voxel or patient data in order to determine said tinnitus condition. The comparing step may utilize machine learning to increase accuracy, for example, by being performed by a processor utilizing machine learning.

The fMRI map may correspond to a portion of said brain of said patient. The fMRI map may correspond to substantially all of said brain of said patient. The fMRI map may be a three dimensional representation of said patients brain over time.

In an aspect, provided is a system for determining a tinnitus condition of a patient comprising: i) a functional magnetic resonance imaging (fMRI) device; and a processor; ii) wherein said fMRI device generates a fMRI map of a brain said patient over a time period; wherein said fMRI map corresponds to a resting state of said patient; and wherein said processor: identifies a plurality of voxels corresponding to regions of said brain of said patient; identifies at least one functional connections between two or more of said plurality of voxels; and analyzes said plurality of voxels in the time domain using iterated integrals to determine a tinnitus condition of said patient.

In an aspect, provided is a method for treating a tinnitus condition of a patient comprising: i) providing a functional magnetic resonance imaging (fMRI) device; ii) imaging said patient with said fMRI thereby generating a fMRI map of at least a portion of a brain said patient; iii) identifying a plurality of voxels in said fMRI map corresponding to regions of said brain of said patient; iv) analyzing said plurality of voxels, thereby determining a personalized tinnitus condition of said patient; and v) treating said patent by providing a therapy based on said personalized tinnitus condition.

The various embodiments and improvements described herein with regard to the method of determining a tinnitus condition may also be applied to and integrated with the system for determining and tinnitus condition aspect and the method for treating a tinnitus condition aspect.

Without wishing to be bound by any particular theory, there may be discussion herein of beliefs or understandings of underlying principles relating to the devices and methods disclosed herein. It is recognized that regardless of the ultimate correctness of any mechanistic explanation or hypothesis, an embodiment of the invention can nonetheless be operative and useful.

BRIEF DESCRIPTION OF THE SEVERAL VIEWS OF THE DRAWING(S)

Figure 1A:
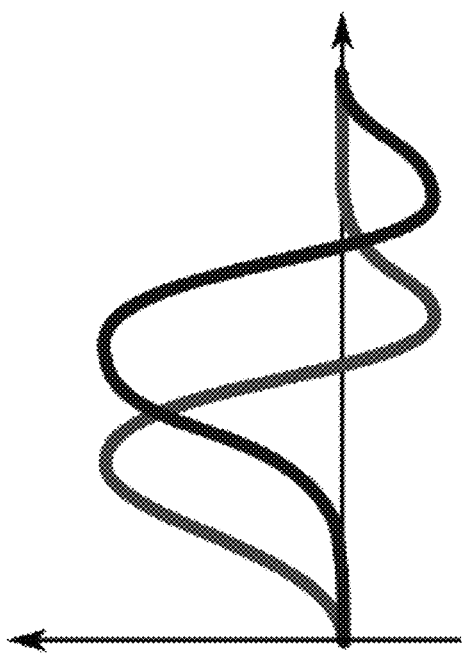

The features, objects and advantages other than those set forth above will become more readily apparent when consideration is given to the detailed description below. Such detailed description makes reference to the following drawings, wherein:

FIGS. 1A-1B. Leader follower relation we would like to capture. Plotting the functions shown in FIG. 1A against each other produces a curve encircling a positive oriented area (FIG. 1B).

Figure 2C:
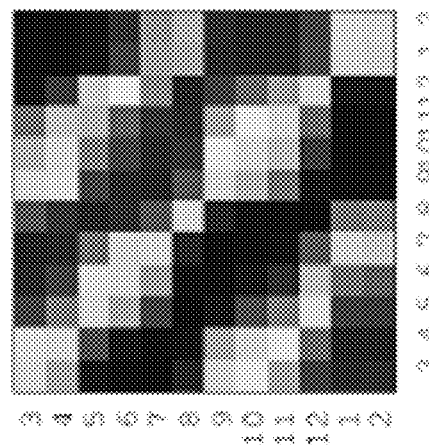
Figure 2B:
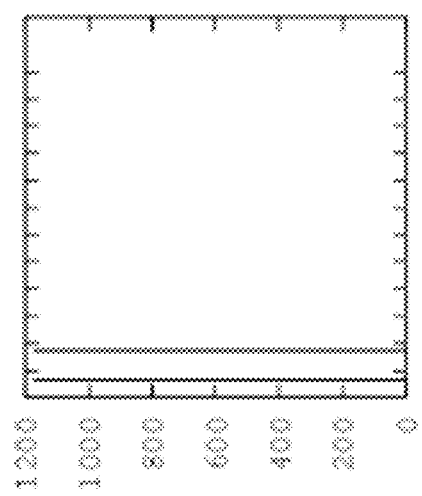
Figure 2A:
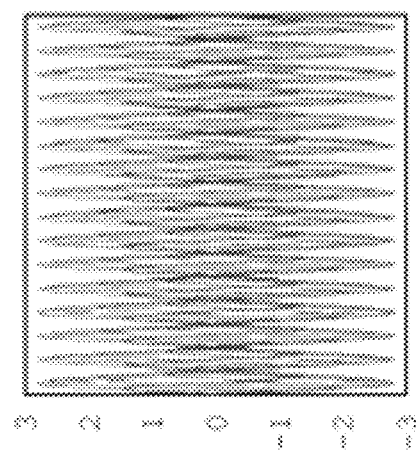
Figure 2E:
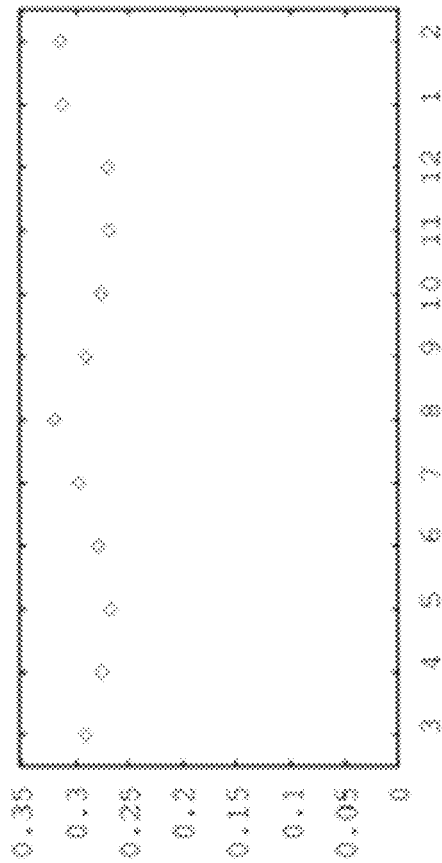
Figure 2D:
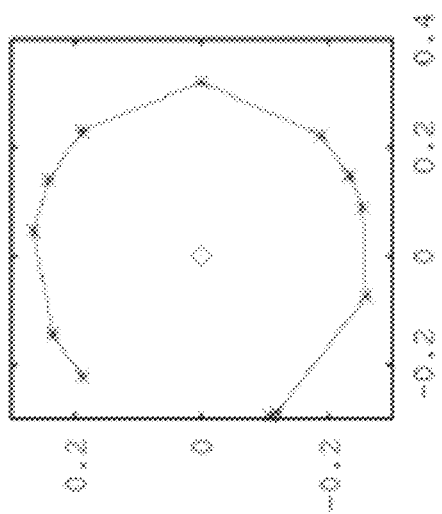

FIG. 2A. Traces of the observations; FIG. 2B: absolute values of the eigenvalues of the lead matrix; FIG. 2C: lead matrix (reordered according to the cyclic order of the phases of the eigenvectors of the lead matrix). FIG. 2D. The components of the eigenvector; FIG. 2E: their absolute values, ordered according to the order of their arguments.

Figure 3C:
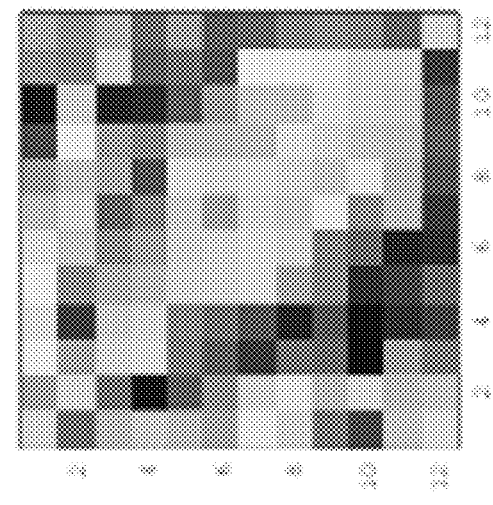
Figure 3B:
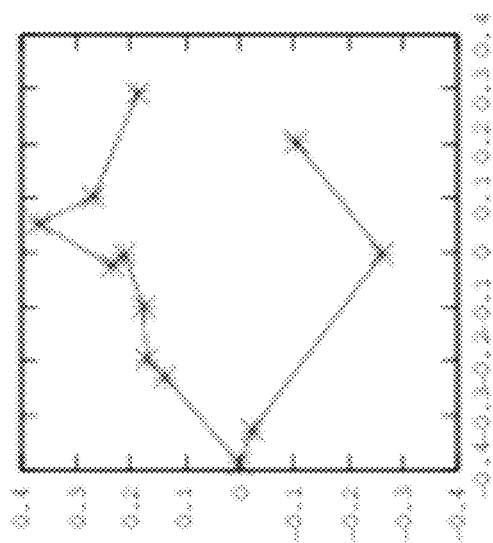
Figure 3A:
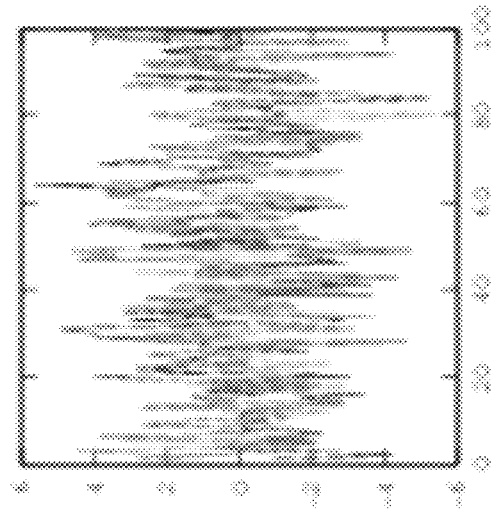
Figure 3D:
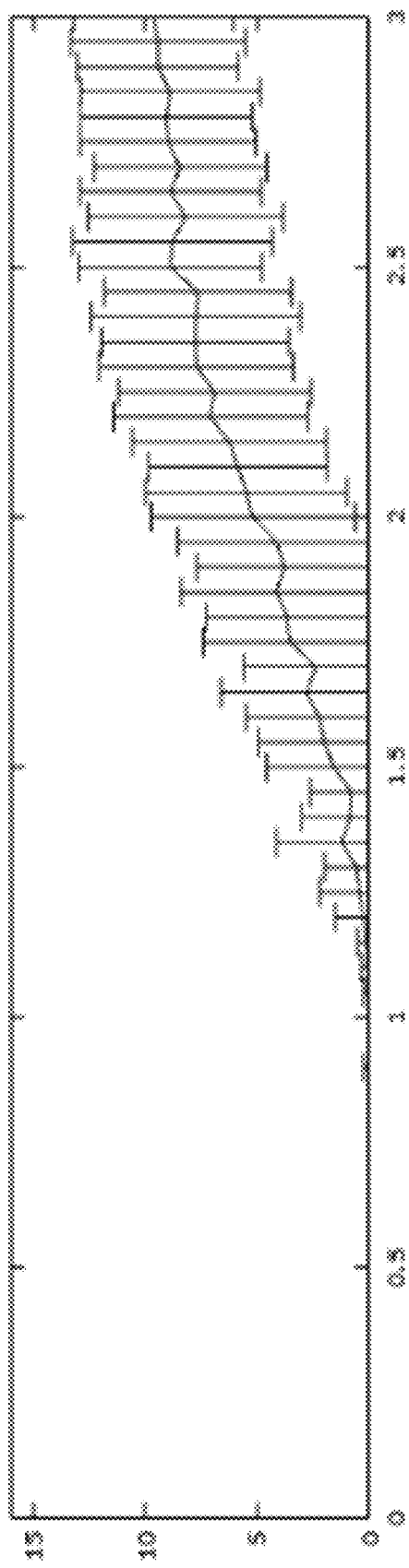

FIGS. 3A-3C. Cyclicity algorithm output for noisy data with Gaussian noise added. (Explanations of the plots are given on the caption of FIGS. 2A-2E.) FIG. 3D. Dependence of the distance of the cyclic permutation recovered by the cyclicity from the true one on the error levels (x-axis representing the noise to-signal ratio).

Figure 4:
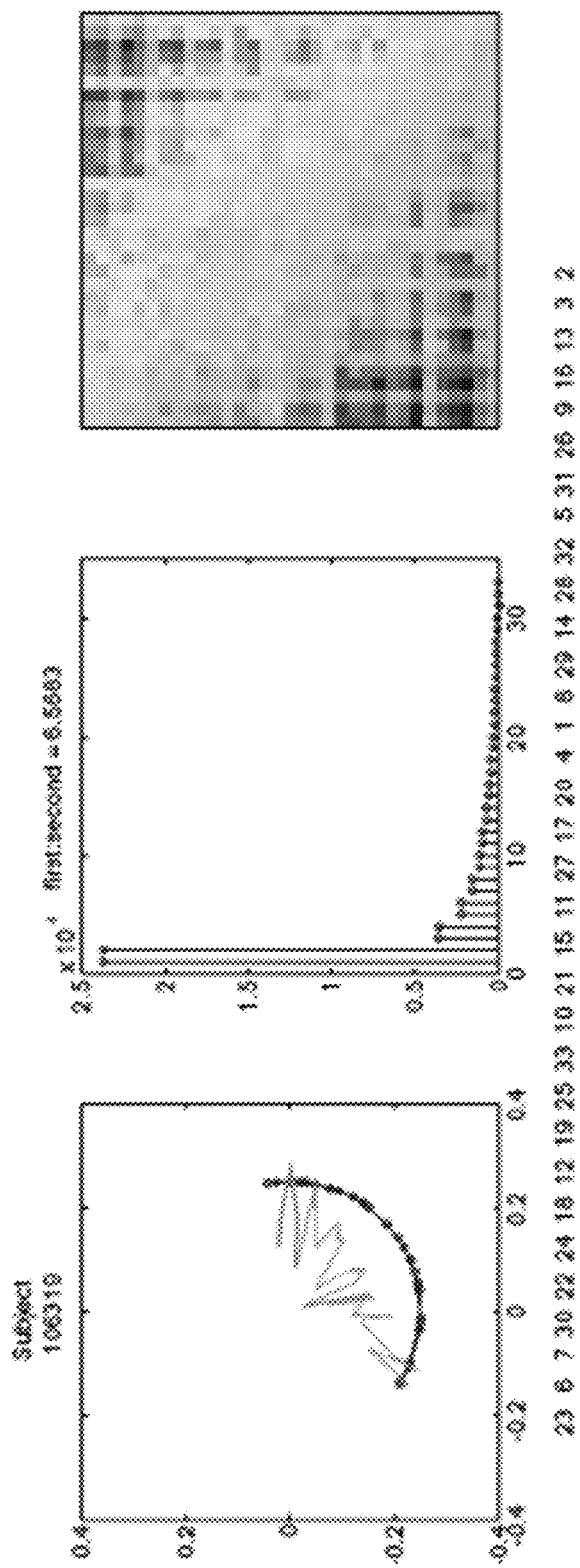

FIG. 4. Results of cyclicity analysis for one of the subjects of the study with well pronounced cyclic signal.

Figure 5:
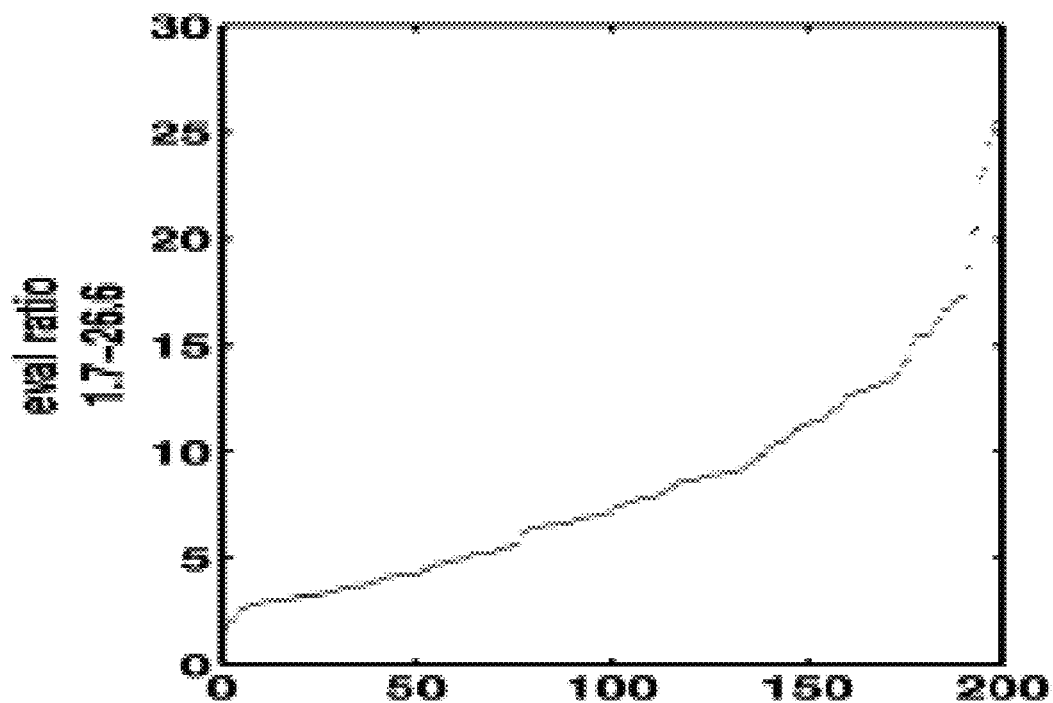

FIG. 5. Cumulative distribution of the number of subjects with the ratio of the leading and next in size absolute values of the eigenvalues.

Figure 6:
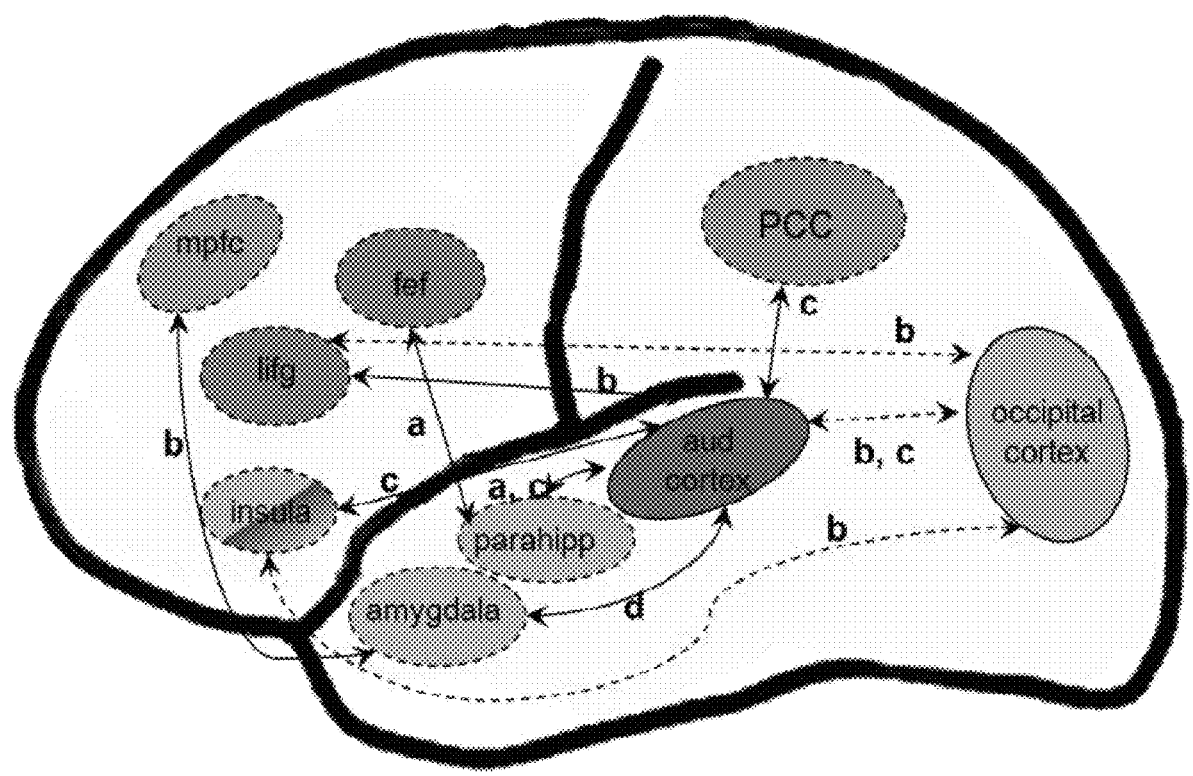

FIG. 6. Summary of main results of resting-state functional connectivity studies in tinnitus. The major networks highlighted are default mode network (shown in blue), limbic network (green), auditory network (red), several attention networks (specifically the dorsal attention network and the executive control of attention, shown in purple), and the visual network (in orange). Positive correlations between regions that are stronger in tinnitus patients than controls are shown in solid lines, while negative correlations are dashed lines. Connections are labeled with letters representing the studies in which they were reported, as follows: a) Schmidt et al., 2013; b) Burton et al., 2012; c) Maudoux et al., 2012b; d) Kim et al., 2012. (PCC: posterior cingulate cortex; mpfc: medial prefrontal cortex; lifg: left inferior frontal gyms; parahipp: parahippocampus; and cortex: auditory cortex; fef: frontal eye fields.) From Husain and Schmidt, 2014.

Figure 7:
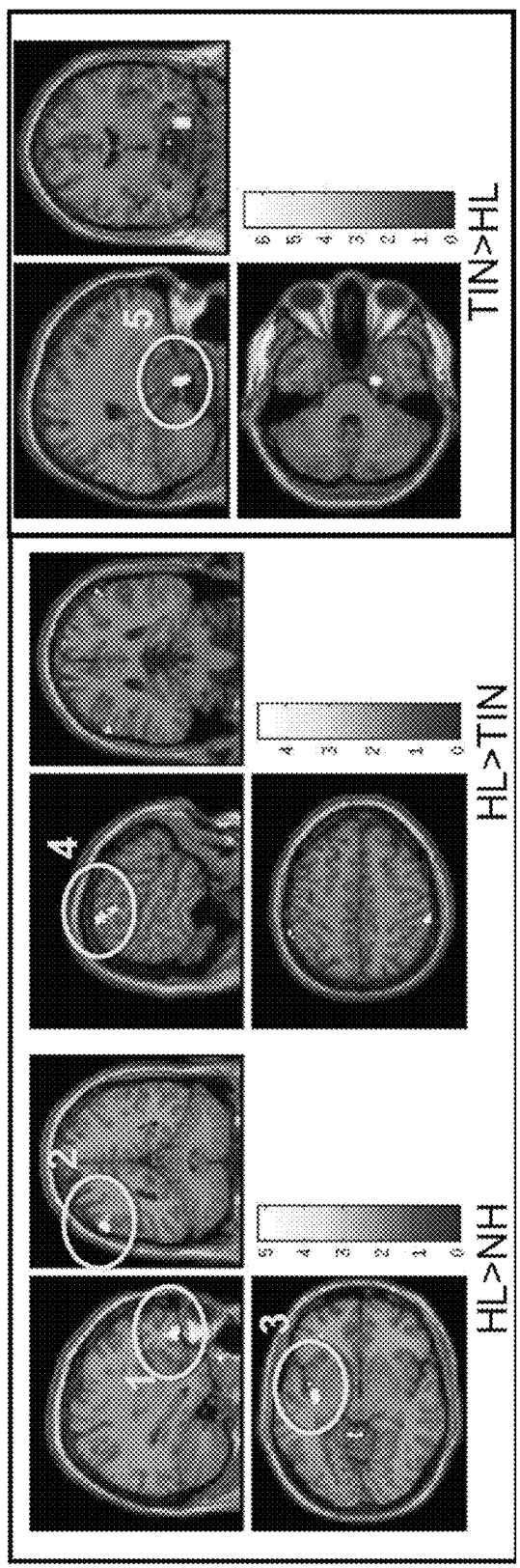

FIG. 7. Differences in connectivity of the dorsal attention network using seeds in the parietal (IPS, intraparietal sulcus) and frontal (FEF, frontal eye fields) cortices. The TIN group shows increased connectivity with the right parahippocampal gyms (5) (part of the limbic system) but reduced connectivity with the other nodes of the attentional system, such as the supramarginal gyms (4). See FIG. 8 for explanation of color bars. From Schmidt et al., 2013. (1) left middle orbital gyms, (2) left inferior parietal lobule, (3) left insula, (4) right supramarginal gyms, (5) right parahippocampal gyms. From Schmidt et al, 2013.

Figure 8:
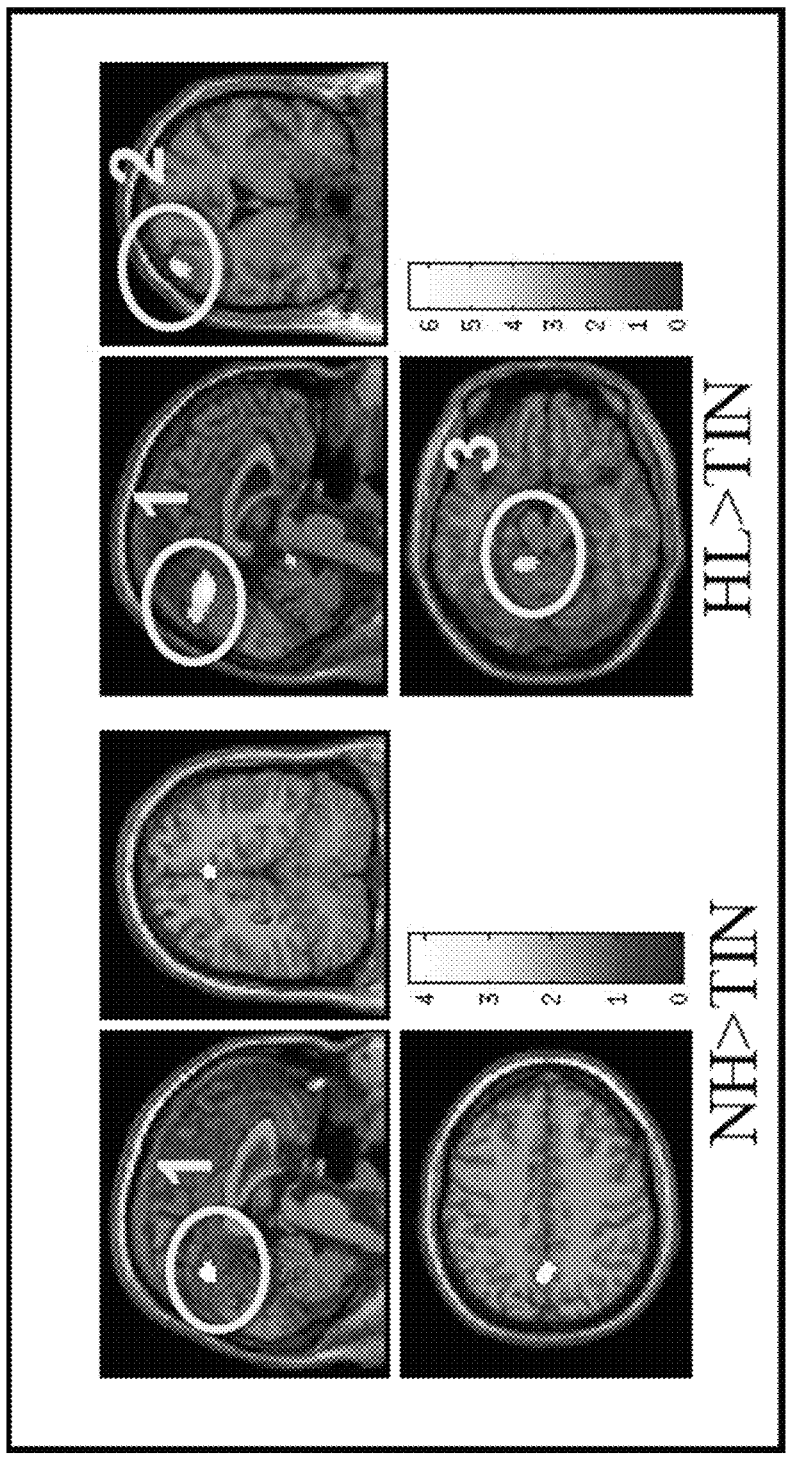

FIG. 8. Reduced connectivity in the default mode network for the tinnitus group compared to the control groups, especially in the precuneus (1), left precentral gyms (2) and left cerebellum (3). The reduced connectivity with the precuneus suggests that the TIN group is not in traditional resting state. Color bars represent t statistics of the statistical parametric maps. From Schmidt et al., 2013.

Figure 9:
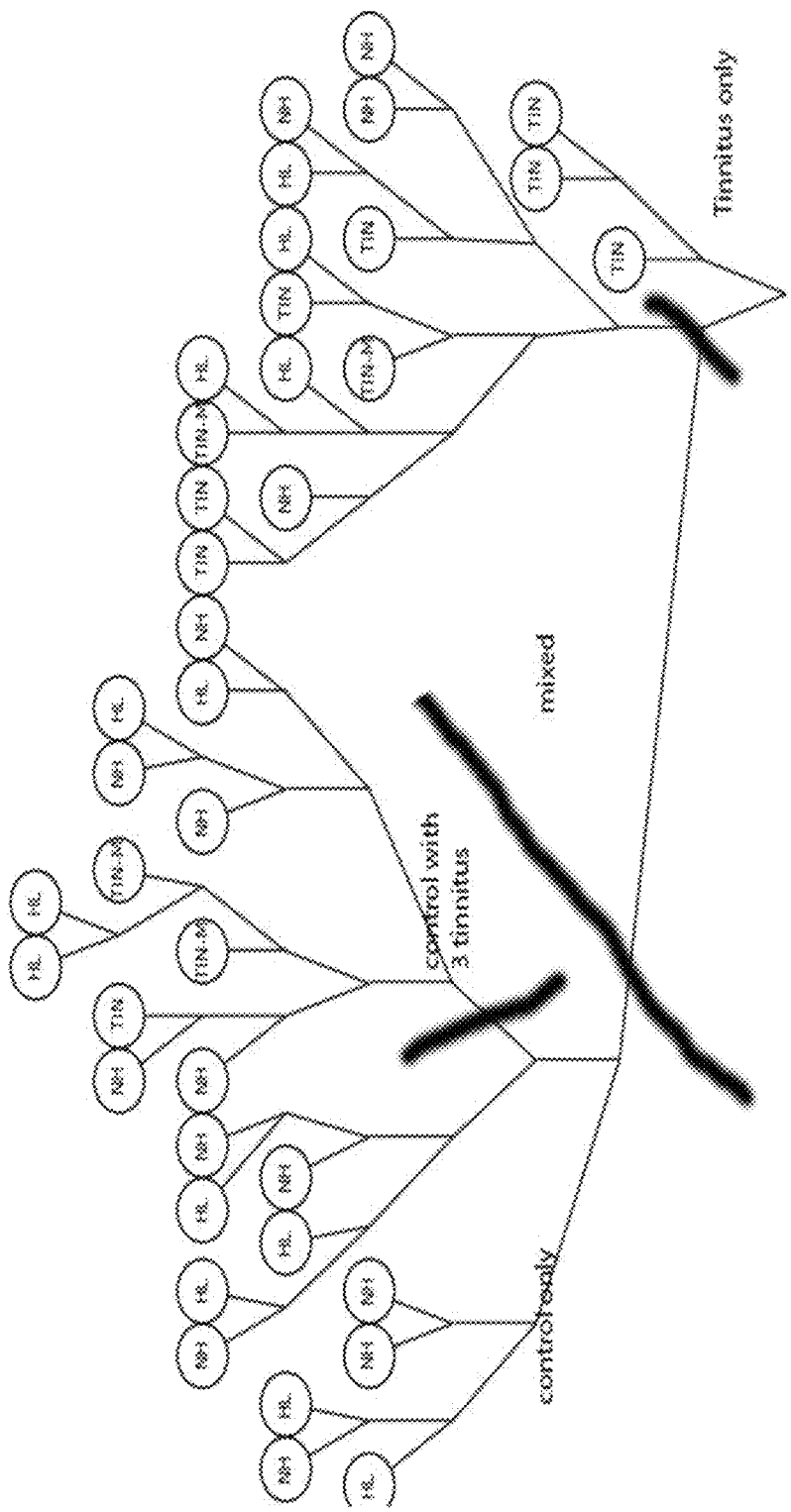

FIG. 9. Example of a clustering tree created via average linkage hierarchical clustering. The tree can be divided into 4 sections marked via black lines (from left to right): branches that are entirely controls, branches that are primarily controls but include some patients, a mixed area, and an area that is all tinnitus patients (right). TIN=tinnitus+hearing loss, HL=hearing loss, NH=normal hearing subjects, TIN-M: patients whose tinnitus was masked during scanning.

Figure 10:
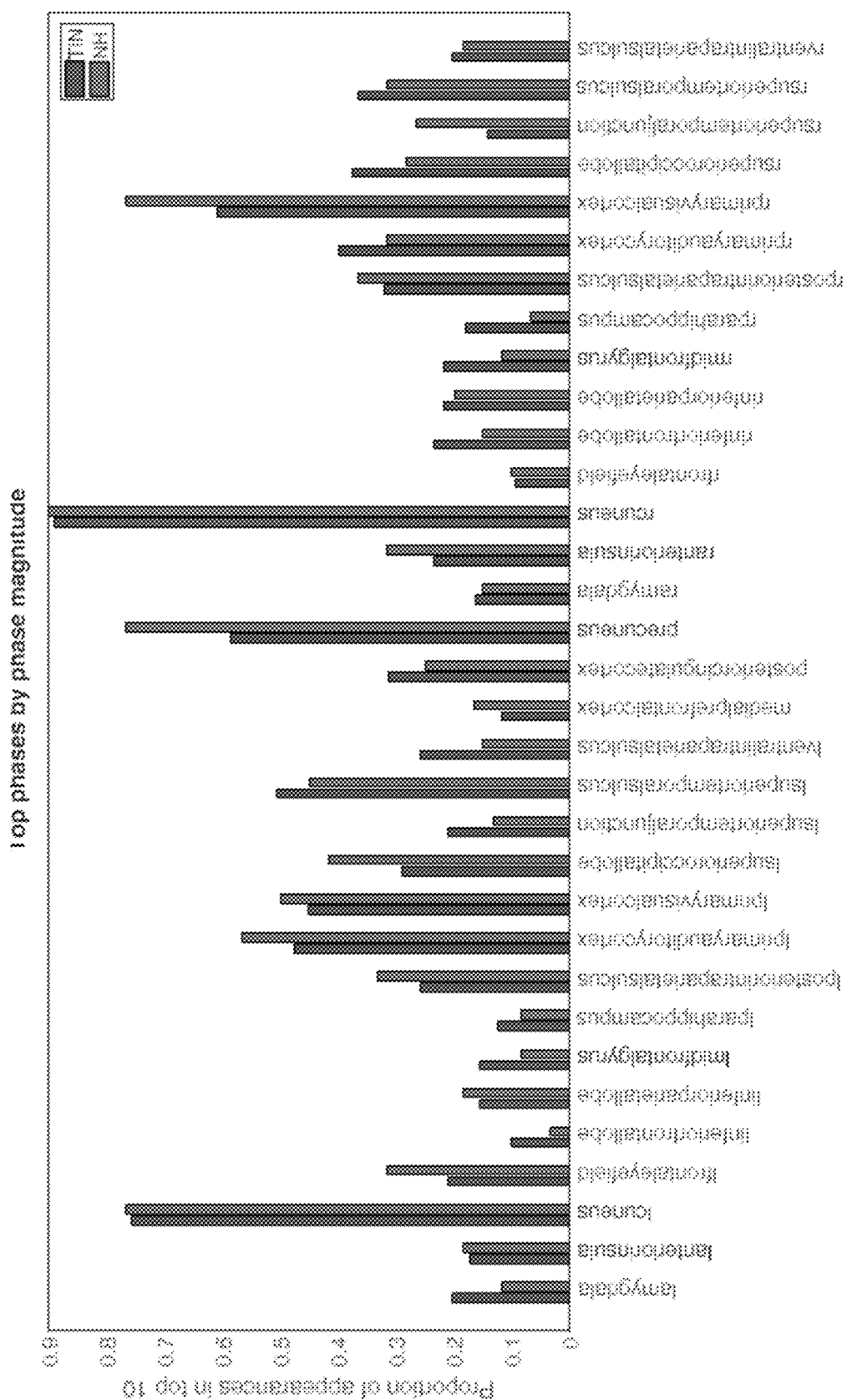

FIG. 10. Regions with the highest magnitudes in the cyclicity analysis. The leading eigenvalue and the corresponding eigenvector of the lead matrix determine the magnitude; in particular, the elements of the eigenvector correspond to ROIs, and the larger an element's modulus is, the greater the magnitude corresponding to the signal from that ROI. The chart shows the proportion of times each region occurred in the top 10 magnitudes for each subject. Bars are displayed for the tinnitus group and the normal hearing controls. This graph reveals that certain regions have consistently high magnitudes in the cyclicity analysis, especially in visual regions such as the right and left cuneus. This is true for both tinnitus and controls. In other regions, such as the precuneus, the phase magnitudes are more variable between groups.

Figure 11A:
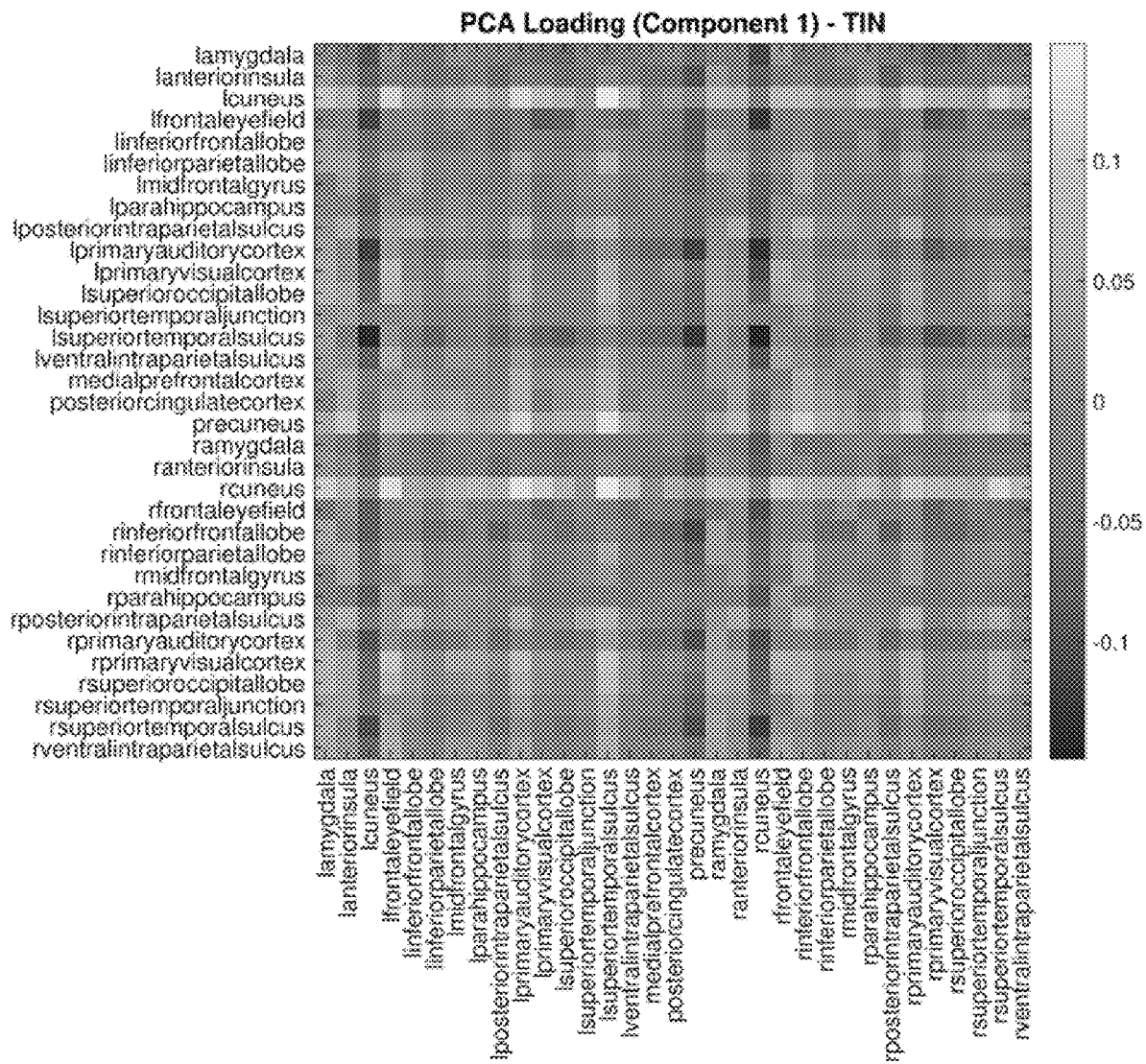
Figure 11B:
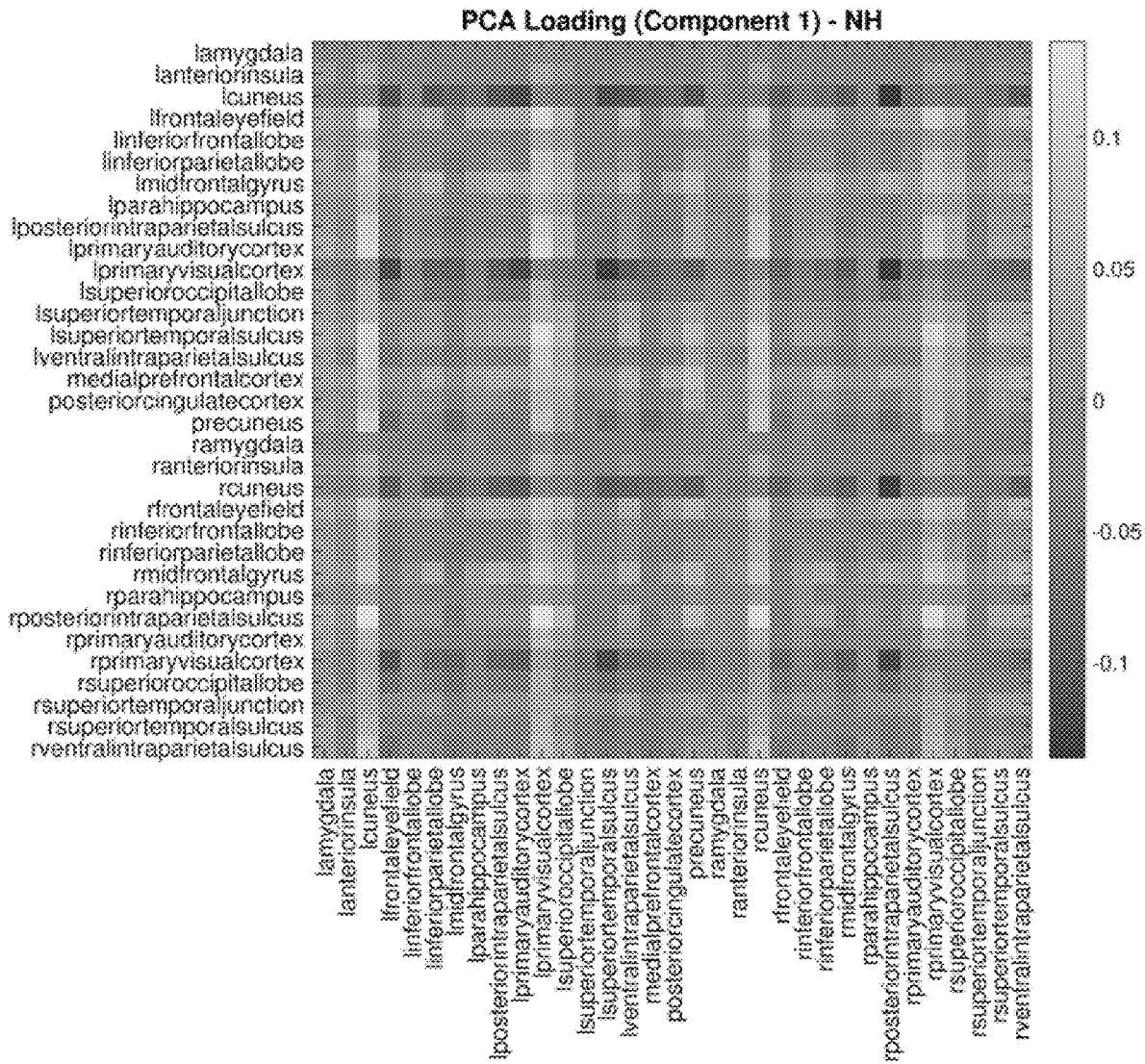

FIGS. 11A-11B. First principal component of each groups' lead matrix. This figure shows the contribution of each ROI pair to the direction of greatest variation in each groups' dataset. This is obtained from PCA and the first loading vector for each group is depicted here. The first component is interpreted as primarily representing cyclic connectivity with the left and right cuneus. Colors correspond to the unit normalized loadings. It is observed that for both the normal hearing controls and for tinnitus subjects the ordering corresponding to the right and left cuneus is strongly determined, whereas the ordering between ROI pairs of other regions is much less evident.

Figure 12A:
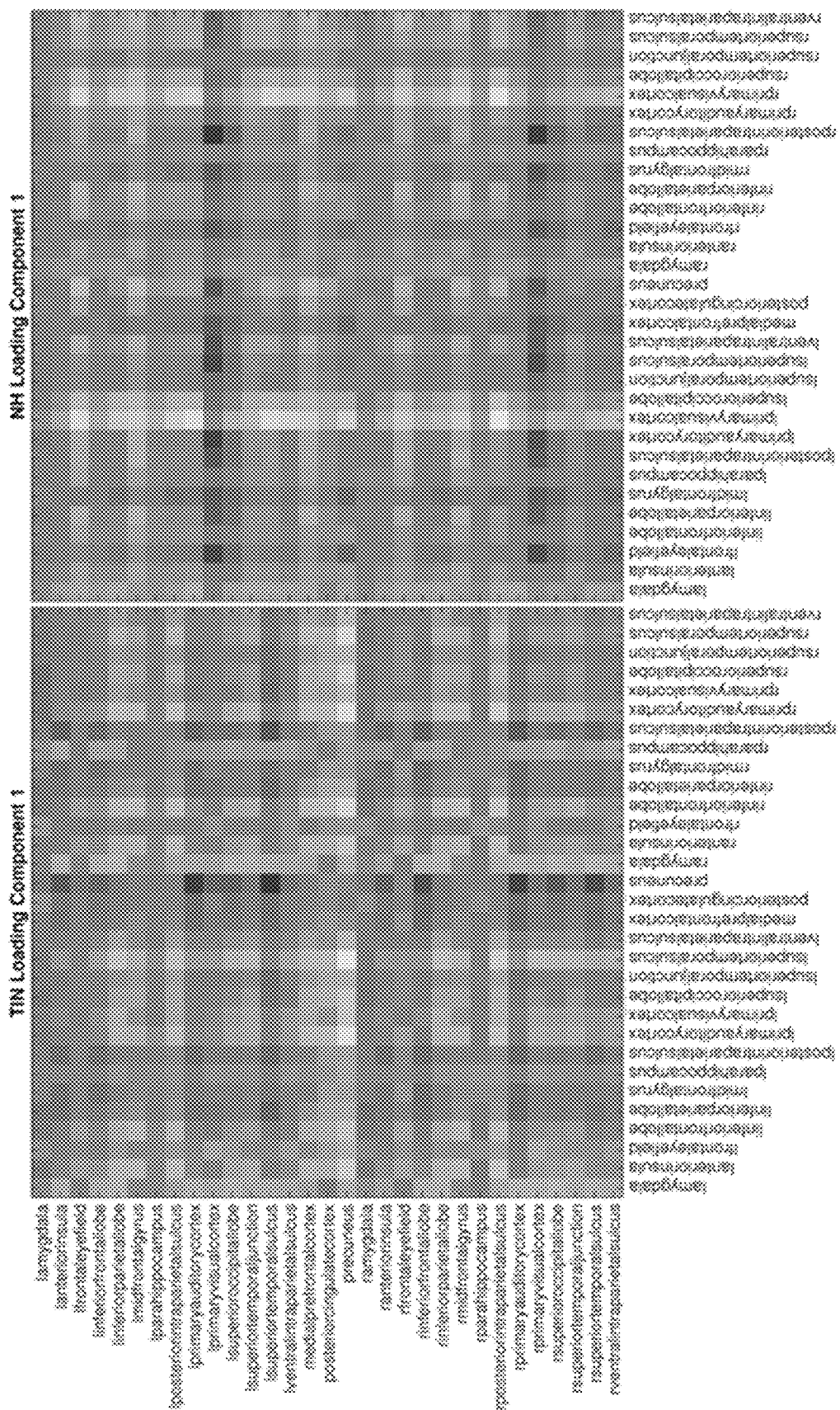
Figure 12B:
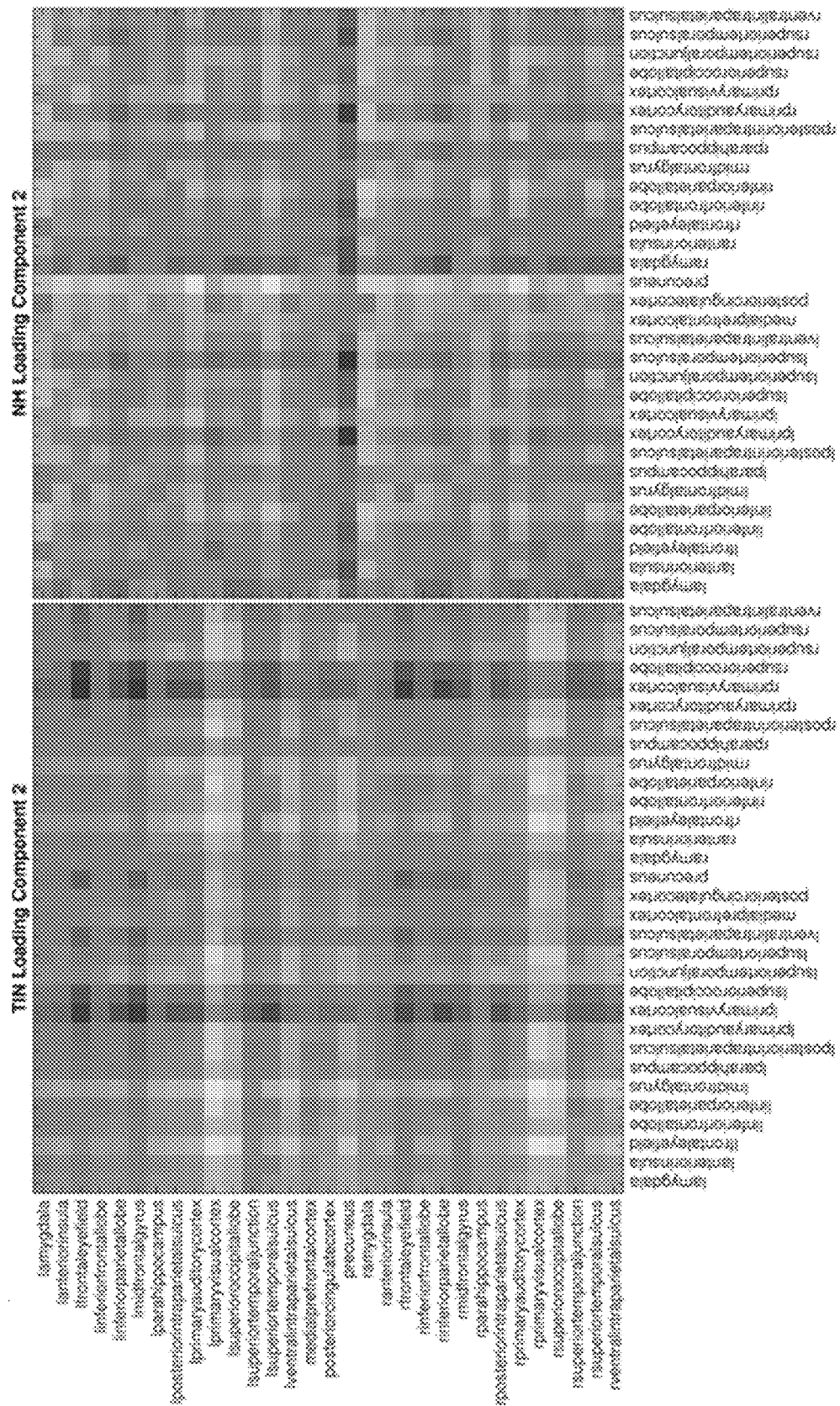

FIGS. 12A-12B. Differences in the first two components of the groups' lead matrices. Similar to FIGS. 11A-11B, here we examine the (FIG. 12A) first and (FIG. 12B) second component loading vectors for tinnitus and normal hearing after removing the right and left cuneus from the cyclicity analysis. The first and second components appear to switch between the two groups. The eigenvalue ratios corresponding to the first two components, $\lambda 1/\lambda 2$, and the first and third components, $\lambda 1/\lambda 3$, for the TIN group are 1.51 and 2.51, respectively, while for NH group the same quantities are 1.97 and 2.84, respectively. Here $\lambda 1, \lambda 2, \lambda 3$ are the leading eigenvalues of the covariance matrix of each group and therefore help quantify how much of the variance is explained by a particular component; a ratio of 1 would mean both components explain variance equally well.

Figure 13:
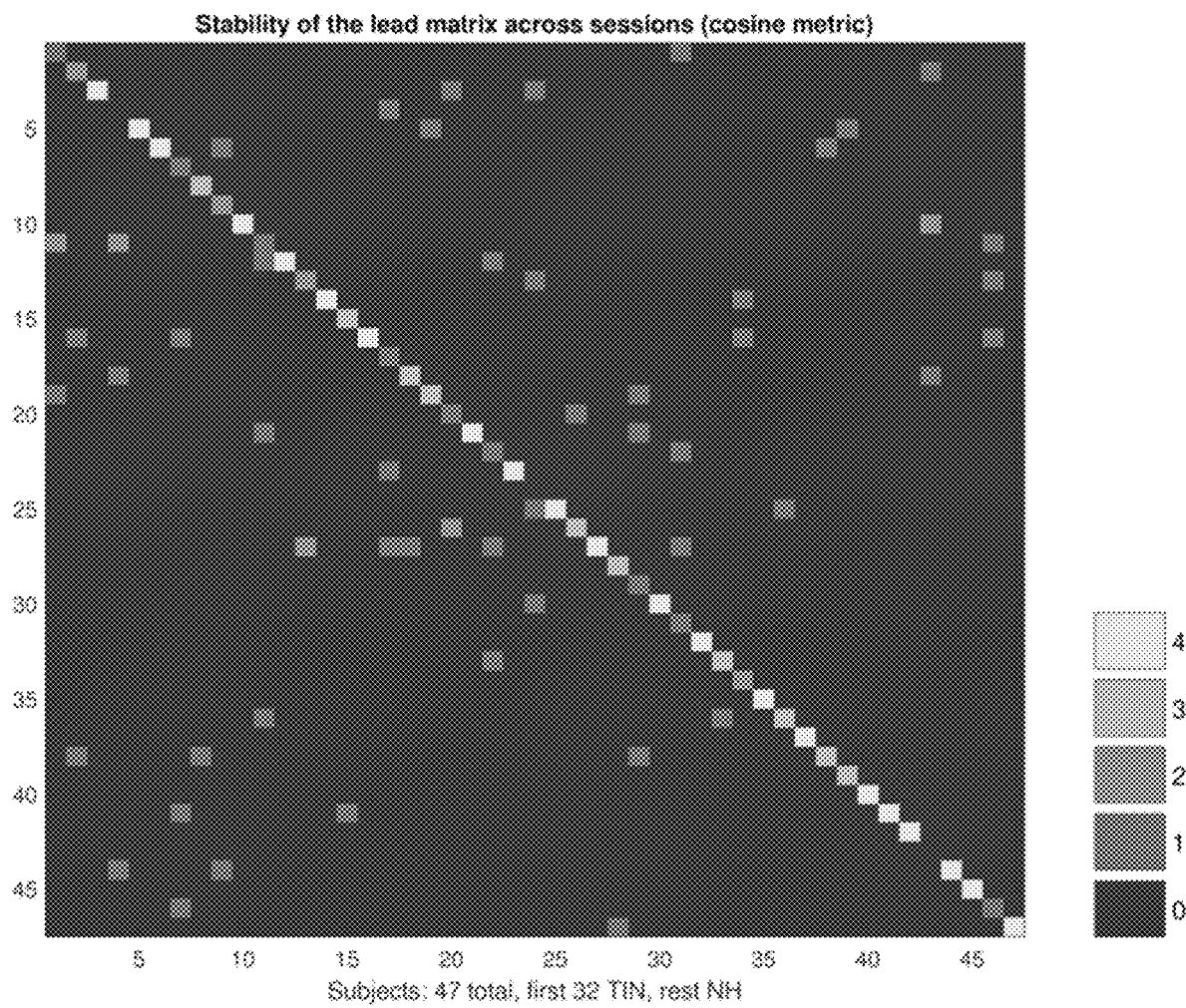

FIG. 13. The stability of the lead matrix across sessions that were 1 week apart. Since the lead matrix is a feature constructed from the fMRI time series data, its consistency over time is investigated here. The figure above is a visualization of the confusion matrix arising from a classifier. Each row and column correspond to an individual subject in the analysis. The colors correspond to how many runs (out of 4 total runs) were correctly classified after training a 1-nearest neighbor classifier with the cosine metric on the other weeks data. The cosine metric serves as a measure of how closely aligned vectors are in high dimensional spaces. This graph shows good stability in the cyclic patterns of data, that is, consistent leader-follower relationships between ROIs, within subjects across 1 week.

Figure 14:
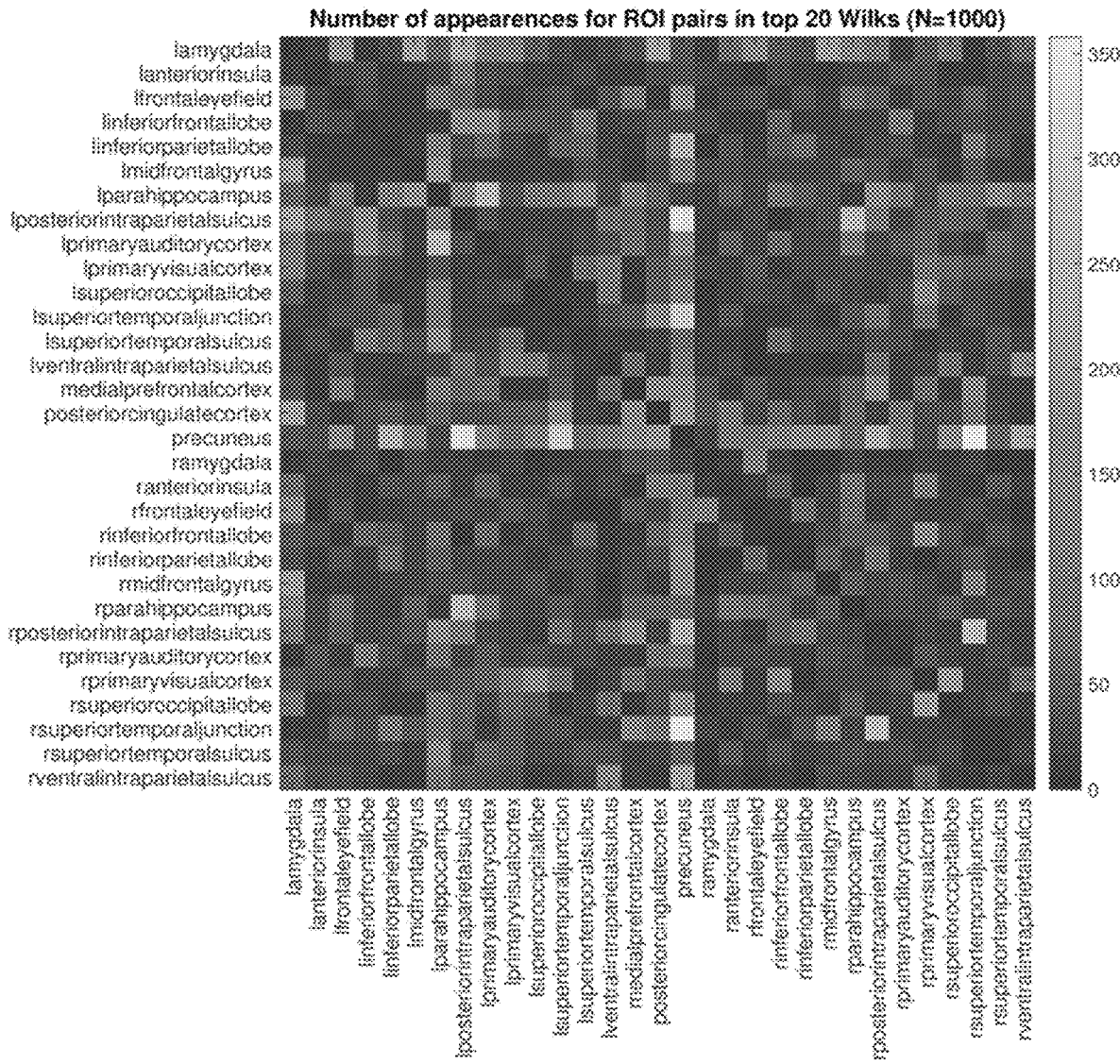

FIG. 14. The most stable ROI pairs with respect to discriminatory ability across the dataset. The Wilks' lambda criterion can be used to determine which features in the data have more discriminatory ability for classification. A thousand random and equally sized subsets of the data were examined, and the top 20 ranked ROI pairs (with respect to discriminatory ability) were recorded. FIG. 14 shows how many times an ROI pair appeared in the ranking.

Figure 15:
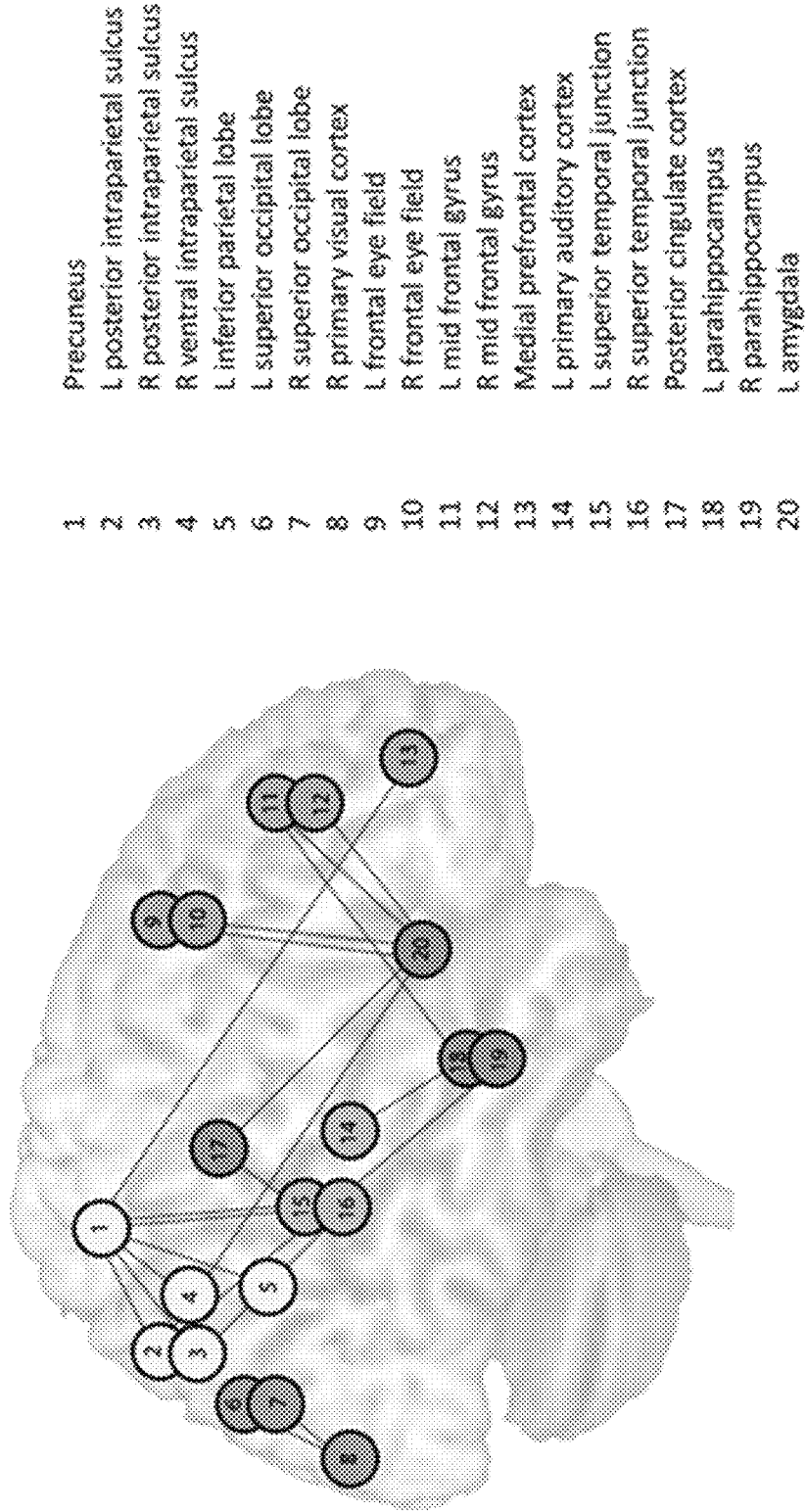

FIG. 15. Graphical representation of the 20 most discriminating ROI pairs that help distinguish TIN from NH.

Figure 16:
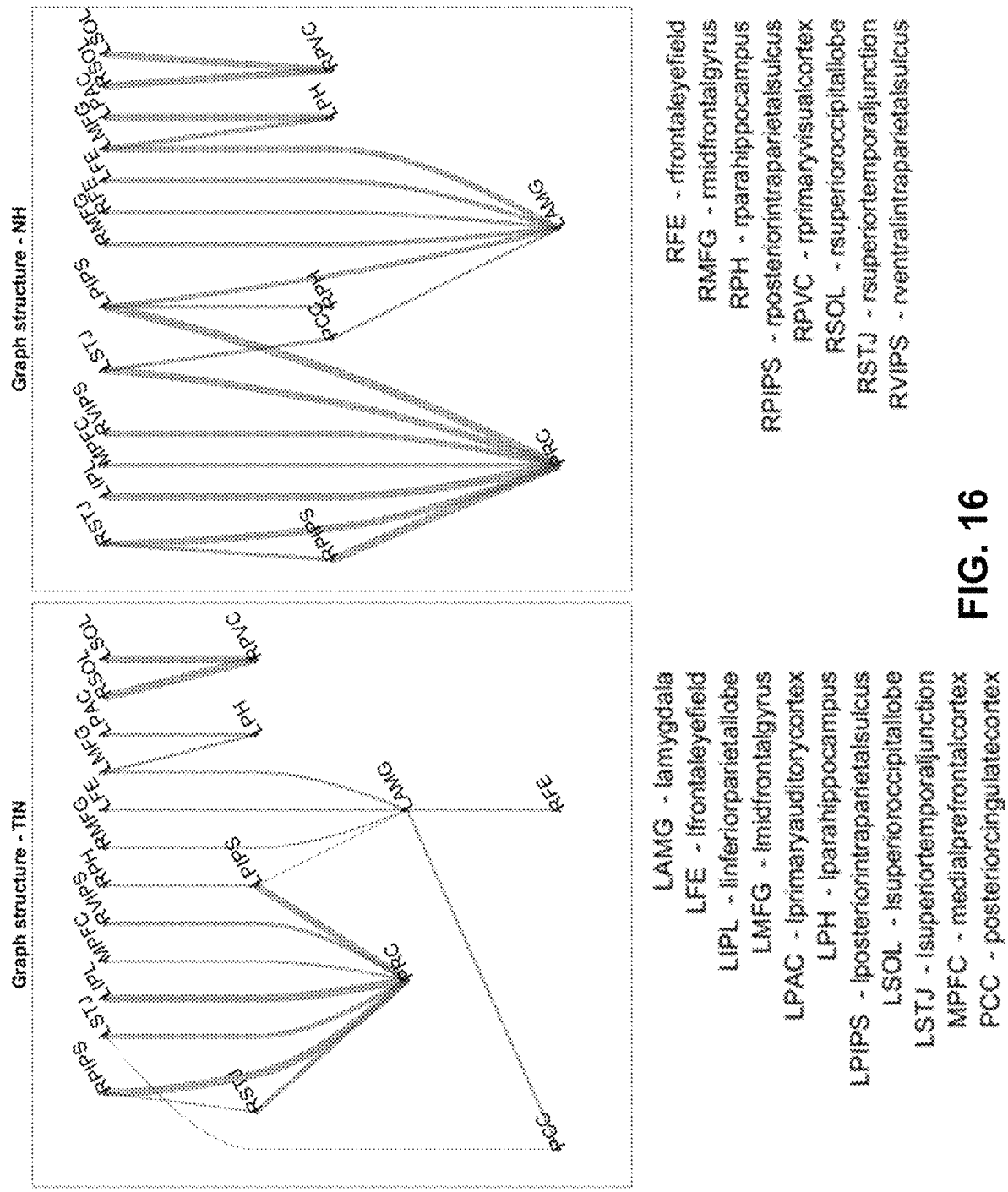

FIG. 16. Graph structure of leader-follower connections. This figure shows the direction of leader-follower relationships between 20 ROI pairs that most help discriminate the normal hearing controls from the tinnitus subjects (activity follows downward). A node is assigned to each layer as soon as possible provided its predecessors have already appeared. The thickness of the edges corresponds to the proportion of subjects with that direction, and thus reveals the consistency of the leader-follower connections. In normal hearing subjects, there is more consistent cyclic connectivity with the amygdala than in the tinnitus subjects.

Figure 17:
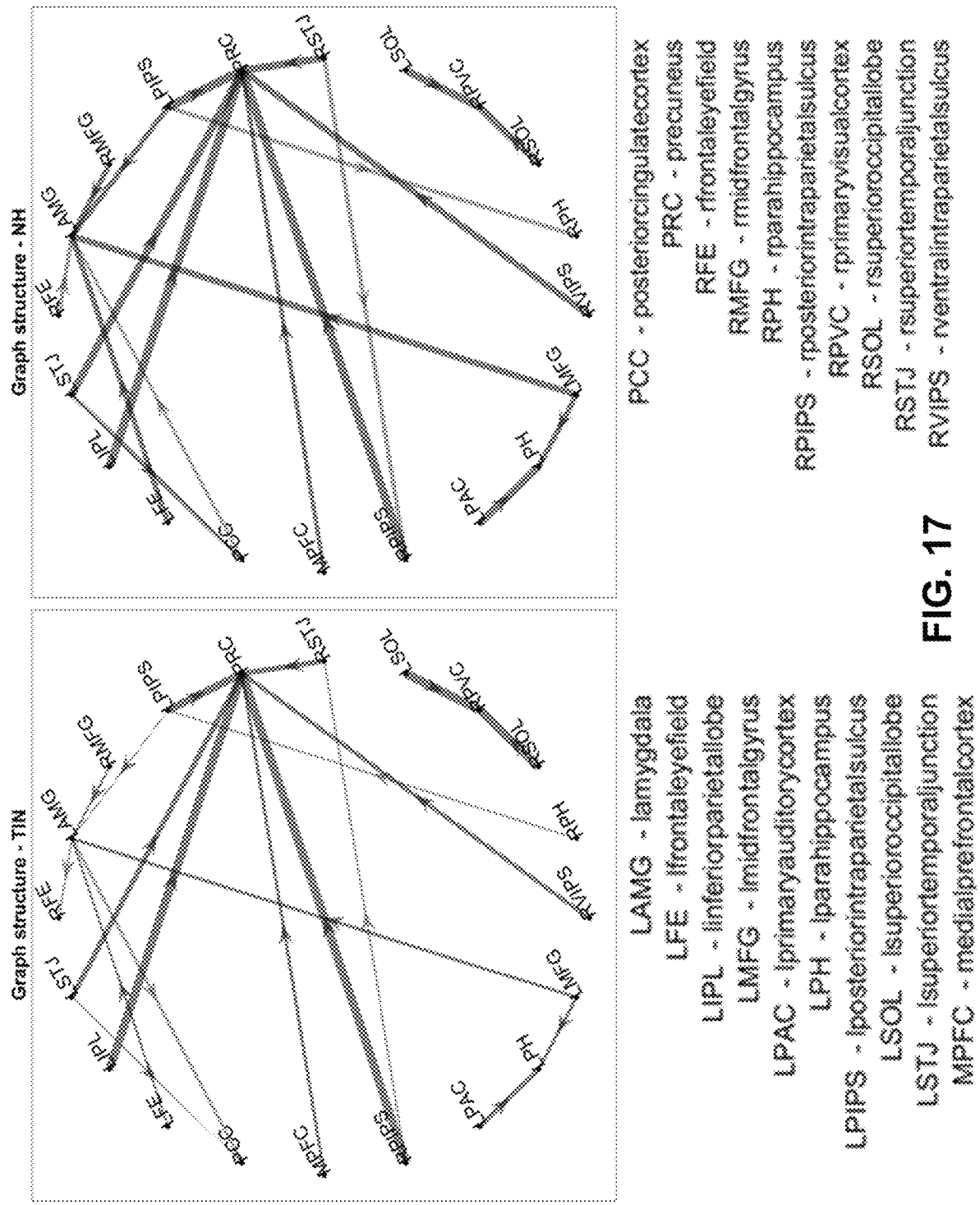

FIG. 17. Differences in leader-follower direction between groups. This graph shows the same data as the previous figure, but fixes the node positions relative to each other for easy comparison and highlights the ROI pairs where the leader-follower relationship switches direction between the two groups.

Figure 18:
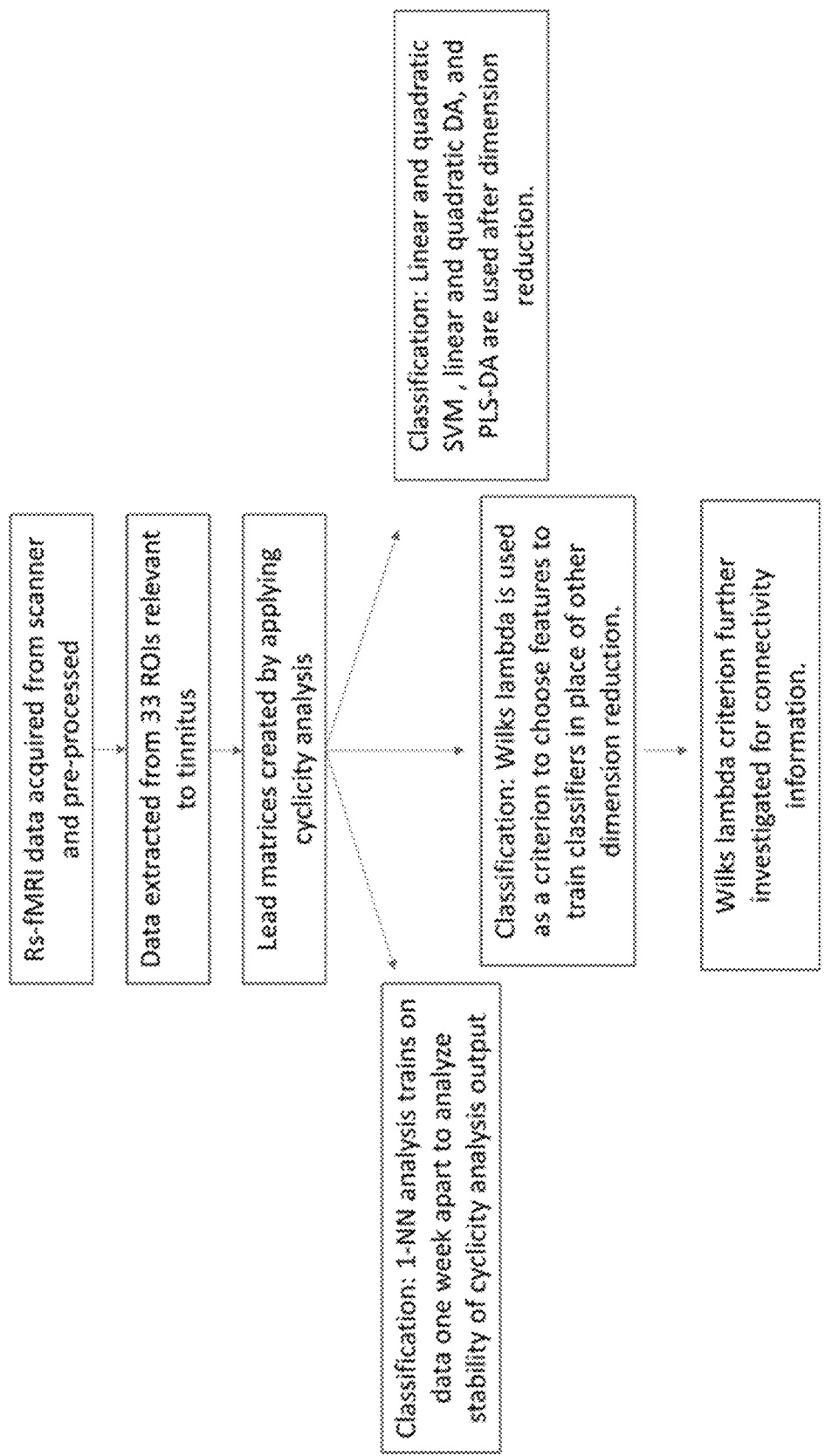

FIG. 18. Schematic of the analysis steps. Resting-state fMRI time-course data is collected, pre-processed, and averaged in relevant ROIs. Then the cyclicity analysis is completed on the data to extract subject lead matrices. These lead matrices were used for three different types of classification. The nearest neighbor algorithm reveals the strength of the stability of a subject's lead matrix. Classification methods are attempted after dimension reduction with PCA or through PLS-DA with 20 features. The Wilks' lambda is used as a criterion to preselect ROI pairs to use in classification. These ROI pairs that help distinguish tinnitus subjects from controls are further investigated.

Figure 19A:
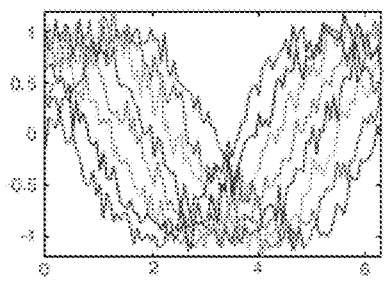
Figure 19A:
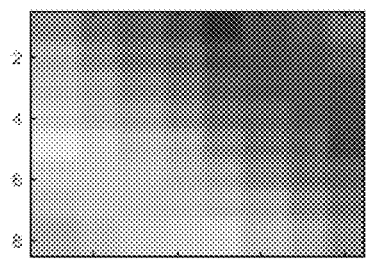
Figure 19A:
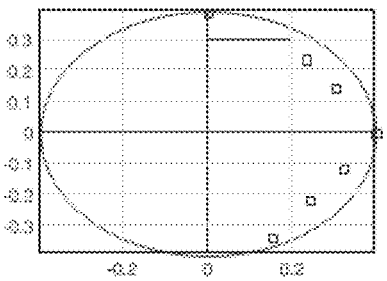
Figure 19B:
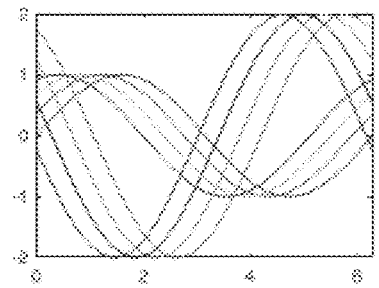
Figure 19B:
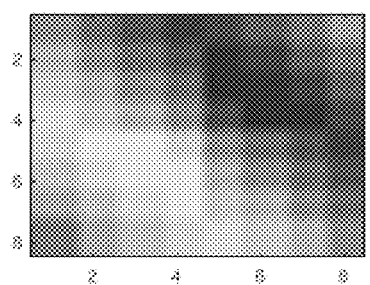
Figure 19B:
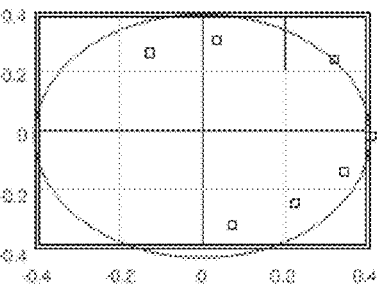
Figure 19C:
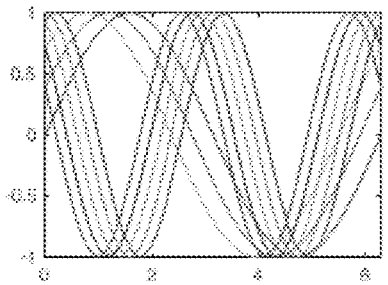
Figure 19C:
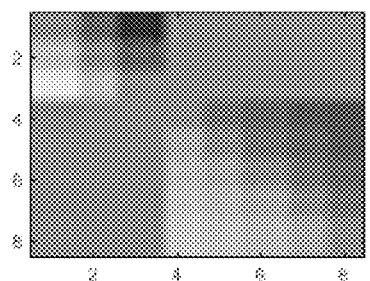
Figure 19C:
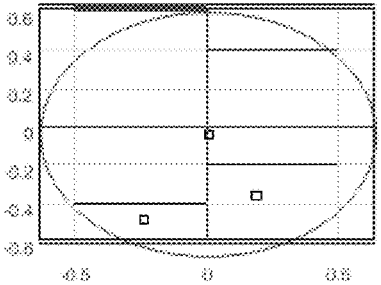
Figure 19D:
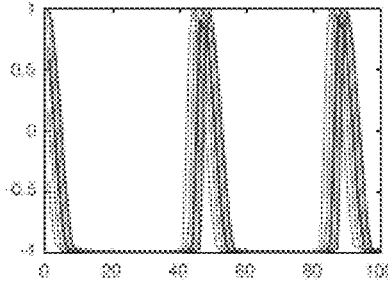
Figure 19D:
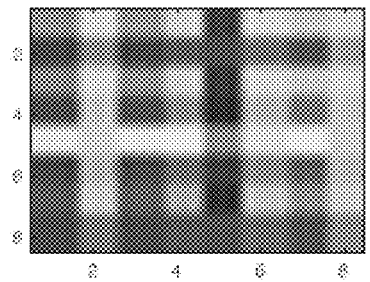
Figure 19D:
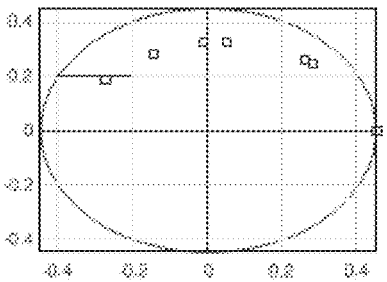

FIGS. 19A-19D. Panel showing how to interpret the lead matrix and phase components. FIG. 19A shows eight phase-shifted sinusoids that have added white noise with SNR=20, the lead matrix obtained from it as well as approximate phase offsets recovered from the first principal eigenvector. FIG. 19B shows two set of sinusoids in a similar fashion, but with one set having different magnitude and being offset from the other set. FIG. 19C shows a signal containing two harmonics, which requires the use of two principal eigenvectors to recover phases completely; note how the lead matrix has an added zero component (the second harmonic is twice the first) giving a point at the origin. FIG. 19D contains a traditional cyclic but aperiodic signal and its corresponding results.

DETAILED DESCRIPTION OF THE INVENTION

In general, the terms and phrases used herein have their art-recognized meaning, which can be found by reference to standard texts, journal references and contexts known to those skilled in the art. The following definitions are provided to clarify their specific use in the context of the invention.

"Tinnitus condition," as used herein, refers to a diagnosis of tinnitus in a patient. Tinnitus condition can be the presence or absence of tinnitus in a patient, for example, to determine if the patient is suffering from tinnitus or some other condition, or if the patient may be untruthful in the assertion that they have tinnitus. Tinnitus condition may also refer to a degree or severity of tinnitus in a patient, including, for example, making a distinction between or more types or causes of tinnitus or evaluating a stage of progression of tinnitus or tinnitus symptoms. Tinnitus condition may also refer to other symptoms or conditions are result from tinnitus (e.g. depression, anxiety, etc.). Additionally, tinnitus condition may refer to a reduction of tinnitus or tinnitus symptoms in response to a treatment in order to evaluate the success or efficacy of the treatment.

"fMRI map" refers to an output from a functional magnetic resonance imaging device. fMRI map may refer to raw MM data including electronic or digital signals as generated from performing an fMRT on a patient. fMRI map may also refer to MRI data that has some degree of processing, for example, converted into an image or three dimensional model wherein the measured parameters (e.g. blood flow activity) are described either numerically or graphically (e.g. as an intensity map). fMRI maps may be processed or analyzed by the various methods described herein.

"Voxel" refers to a point or three-dimensional volume that describes or corresponds to a specific position within three-dimensional space. Voxel may refer to data collected by an fMRI corresponding to a specific point or volume within a patient's body. For example, a voxel may refer to fMRI data or signals indicating blood flow that corresponds to one or more specific regions of a patient's brain. A voxel may have a time component wherein other data included in the voxel corresponds specifically to the time in which the data was acquired. Voxels may be processed or analyzed by the various methods described herein.

"Functional connection" refers to a relationship or link between two or more voxels. Functional connections generally refer to complex brain responses that effect more than one area of the brain (corresponding to voxels). Functional connection may refer to a relationship between any number of specific voxels. Functional connections may be analyzed or processed in similar ways as voxels.

The following examples further illustrate the invention but, of course, should not be construed as in any way limiting its scope.

Example 1

Diagnosis of Tinnitus Using Cyclic Multivariate Time Series

Described herein is a novel, reparametrization invariant method of recovery of cyclic patterns in multivariate time series. Basics of the analysis are outlined, and applications to fMRI traces are shown. When tested on a widely used dataset of measurements of human subjects in resting state, the data shows presence of an exogenous auditory stimulus driving the results.

Summarizing, our techniques reveal strong patterns of cyclic behavior in the brain activities in a significant fraction of the population studied. On the other hand, the results indicate a challenge to the assumption that the measurements captured are dominated by the resting state activity. We remark that the detrimental effects of the equipment noise in the fMRI studies has been recorded in the literature, see [11].

Resting state functional connectivity is defined as inter-regional correlations of spontaneous brain activity, which can be reliably organized into coherent resting state networks. The networks thus identified are similar to the networks that appear during a task. Although baseline activity can involve any brain region, the default mode network has gained prominence as the canonical resting state network. It is most active at rest and exhibits reduced coherence when the participants are engaged in goal-directed behavior or perform tasks involving attention (Shulman et al., 1997). An opposite pattern is seen with other networks (e.g., auditory), which exhibit heightened, correlated activity in the task-based state but retain connectivity (although with reduced activity) during rest. These resting state networks have been shown to be altered in tinnitus patients (Husain and Schmidt, 2014), and resting state fMRI shows potential as a useful tool in the study of tinnitus.

There are several advantages to using resting-state functional connectivity to study tinnitus. Data collection is efficient and not demanding of participants. In addition, tinnitus is uniquely suited to being studied using a resting state paradigm because of its subjective nature—there is no task-based modulation of the tinnitus signal. At the same time, perception of a chronic internal noise may place the person in a task-based state and no true resting state may be achieved by individuals with tinnitus. However, this and other alterations to functional connectivity can help dissociate tinnitus patients from controls. Resting state functional connectivity lends itself to be used for subtyping of various groups and differential diagnosis, and it has been used in this way to examine, for example, schizophrenia (Greicius, 2008, Karbasforoushan and Woodward, 2012) and aging (Greicius et al., 2004, Chen et al., 2011, Agosta et al., 2012, Koch et al., 2012). It has the potential to relate behavioral measures, such as tinnitus severity, and comorbid factors, such as hearing loss, with specific neural networks.

Cyclicity and Periodicity

The distinction between the cyclic and periodic phenomena is important. Periodicity of a process does imply cyclicity, but not vice versa—there are plenty of processes that are manifestly cyclic, but not periodic, in the sense that no time interval, i.e. period P can be found such that shift of the process along the time axis by P leaves it invariant. Examples of cyclic yet not periodic processes include cardiac cycle; muscle-skeletal complex movements exercised during a gait; population dynamics in closed ecosystems; business cycles and many others. It is natural also to look for cyclic phenomena in the mental activity.

This work aims at the introduction of several interconnected computational tools for understanding cyclic phenomena, which are explicitly reparametrization invariant. While we outline the key results and algorithms underlying these techniques, the complete presentation of the cyclicity toolbox will be done elsewhere [1].

Dynamic Functional Connectivity Problem

Dynamic patterns of functional connectivity present several challenges to data analysis, especially for the problem of the resting state connectivity [14].

Until quite recently, the sampling rate of the brain activity signals was low, and the data comparatively noisy which led to (tacit) assumption that there is little dynamical changes in the signal interrelationships within the measurement window.

The so-called "resting state" of the brain, customarily associated with self-consciousness, the processes of mind not triggered by some external stimuli, is one of the most exciting paradigms of the modern neurophysiology. The emergence of functional magnetic resonance imaging, tracking the levels of oxygen carried to the brain cells as a proxy for the activity signals, became the de facto standard of the resting state studies, see [8]. It is not surprising therefore, that in an attempt to understand the spatio-temporal patterns of brain activity in the resting states, the researchers turned to tools allowing more granularity in the time domain. Most of the work in the area pursued rather traditional venues of time series analysis (correlations, information theory based metrics), somewhat limiting the resulting analysis (compare [2], [9]).

The prevalent techniques of detecting dynamics patterns in fMRI traces rely heavily on some a priori filtering, such as the sliding window analysis [10]. Despite several successes, these methods suffer from heavy dependency of the results on the parameters of the smoothening procedure: too short a window fails to suppress the noise enough, and too long a window risks filtering out the actual dynamics of the resting state processes, characteristic frequencies of which are still not characterized.

With this background, the techniques that are explicitly designed to be time-reparametrization invariant, are ideally suited for analysis of the processes without a base frequency, or aperiodic, if cyclic. Recovery of the intrinsic connectivity networks should be significantly enhanced by such tools.

Phenomena Cyclic and Periodic

The challenge of uncovering the dynamic patterns of default functional connectivity network is one of many examples of problems dealing with analysis of phenomena that are cyclic yet not periodic.

In common usage, the notions of being cyclic and periodic are often used interchangeably, and for a reason: any cyclic phenomenon, that is one whose underlying state space is a circle $C \cong \mathbb{S}^1$, can be lifted to a periodic phenomenon on the state space $T \cong \mathbb{R}^1$ which is the natural (universal) covering of C. The domain and the range of the mapping $\mathcal{T}:T\to C$ can be parameterized in a consistent way, so that any two points in T separated by the period P are mapped into the same point of C. Equivalently, this amounts to the representation of the circle as $C \cong \mathbb{R}/P\mathbb{Z}$. In other words, any process whose evolution can be described as traversing a cycle, can be made periodic by an appropriate coordinate change on the T.

We will be referring to any such parameterization of C as the internal clock, and the consistent parametrization on T as the internal time, reserving for the points of C the name internal state. In internal clock, the process is necessarily periodic.

The implications of this absence of a periodic (in physical time) representation of a cyclic phenomenon are relevant. For periodic phenomena a powerful mathematical tool—Fourier analysis (and its numerous versions, such as Laplace, cosine transforms, operator calculus, etc.)—is readily available. However, it depends critically on the structure of the time space as a homogeneous space of the groups of shifts. The fact that the (abelian) group of shifts acts on the timeline, leaving the law of the observable functions invariant means that these functions admit a representation as a linear combination of the characters of the group of the shifts of time, that is eigenfunctions of the shift operator, that is the exponential functions.

All of these mechanisms are absent in the case of cyclic but non-periodic functions, and a new conceptual foundation for recovering and understanding cyclicity without relying on the periodicity is needed.

Reparametrizations

Consider an arbitrary parametrization of the internal clock, $$R: \mathbb{R}^1 \to T, \quad (1)$$

which we will be interpreting as the evolution of the internal clock under the physical time: $R(\tau) \in T$ is the state of the internal clock at (physical) time $\tau$.

A P-periodic function $f:T \to V$ with values in some range V (that is, a cyclic phenomenon) defines unambiguously a function on the internal state space $f:C \to V$. The composition $f \diamond R: \tau \to f(R(\tau)) \in V$ defines a (vector-valued) function; its value is the state of the cyclic phenomenon observed at time $\tau$.

We remark that one should not confuse the cyclicity with quasi-periodicity: quasi-periodicity of a function means that vit is obtained from a function on a torus via pull back of an affine immersion of the real line, thus again, relying on the group structures.

A natural proposal to recover the underlying periodic function f on the internal clock space from observations of $f \diamond R$ is to identify the values taken by the observables thus recovering the internal state space. A version of this idea is to single out special values of $f \diamond R$, for example the critical points of some linear functional of the data. Unfortunately, this procedure is quite fragile and highly susceptible to disruptions by the noise.

Trajectories and Their Invariants

From now on, we will assume that the range of the observed processes is a d-dimensional Euclidean space $V \cong \mathbb{R}^d$, with coordinates $x_j, j=1, \ldots, d$. Before attacking the specific problem of recovering the cyclic nature of the observed processes, we will address the general question, of reparametrization invariant functionals of trajectories: what are the functions of trajectories that do not depend on how one traverses them?

This question is classical, and has an answer in terms of the iterated path integrals, a theory going back to Picard and Riemann, and reintroduced into the modern mathematical practice by K.-T. Chen.

Iterated Integrals

Iterated integrals are explicitly reparameterization invariant functionals of a trajectory. They are defined in an inductive fashion.

Iterated integrals of order zero are just constants, associating to any trajectory $\gamma$ a number $I(\gamma) \equiv c \in \mathbb{R}$. For k>0, the iterated integrals of order k are defined as the vector space generated by the functionals $$I(\gamma) := \sum_{1 \leq i \leq d} \int_{t_s}^{t_t} I_j(\gamma_{t_s,t}) d\gamma_j(t), \quad (2)$$

where $I_j$ are the iterated integrals of order<k.

Iterated Integrals of Low Orders: It is immediate that the invariants of order 1 are exactly the increments of the trajectory over the interval I, Starting at order 2, the iterated integrals render more information than mere increments. By definition, the iterated integrals of order 2 are spanned by the functional $$I_{k,l} = \int_{t_k}^{t_l} \gamma_k(t) d\gamma_l(t). \tag{3}$$

In other words, the iterated integrals of order 2 form a vector space spanned by the (algebraic) areas encompassed by the projections of the trajectory γ onto various coordinate 2-planes. (One might need to close up γ; this can be done, for example, by adding a straight segment connecting starting and ending point of the trajectory. Different choices of closure contribute to I $I_{k,l}$ terms that are iterated integrals of order 1.)

Completeness of the Iterated Integrals: From the construction of the iterated integrals it is immediate that they are invariant with respect to a reparametrization. Also, it is clear that a parallel translation γ ↦ γ+c, e∈V leaves the iterated integrals invariant.

We will call a detour a segment of the trajectory that is backtracked immediately. In other words, if the trajectory can be represented as a concatenation γ=γ$_1$|γ$_2$|γ$_2^{-1}$|γ$_3$, (where j denotes concatenation of the trajectories, such that the endpoint of one corresponds to the starting point of the other, and γ$^{-1}$ is the trajectory traversed backward), then the segment γ$_2$|γ$_2^{-1}$ is a detour.

It can be seen by an inductive argument, that removing a detour does not change any of the iterated integrals.

We will be calling a trajectory without detours irreducible. A generic perturbation of a trajectory with range in dimension higher than 1 makes it irreducible. On the other hand, an irreducible trajectory with values in $\mathbb{R}^1$ is just a monotone function: the theory of iterated integrals relies on the multivariate character of the signals.

The fundamental result of [3] states that the iterated path integrals form a full system of the invariants of irreducible trajectories (defined up to reparametrization) in Euclidean space, up to a translation of the curve:

Two irreducible trajectories γ$_1$, γ$_2$:I→V are equal up to translation and reparametrization if and only if all their corresponding iterated integrals coincide.

In other terms, up to a shift, an irreducible trajectory is characterized by its iterated integrals, which for a complete system of its (reparametrization invariant) parameters.

Leaders and Followers

Completeness of the system of functionals on the trajectories in V given by iterated integrals suggests that any data driven exploration of parametrization-independent features can rely on these functionals as a tool rich enough to extract any information.

We apply this idea to the quest for detection of cyclic phenomena. One of the frequent features of cyclic phenomena is a self-sustained cycling, in which an active process triggers another process, which in turn triggers the next one, and so on, for a cyclic sequence of processes. Examples of such cyclic sequences of activation-relaxation processes are numerous, and include trophic chains [13]; virtuous cycles in innovation dynamics, such as software-hardware coupling [5]; autocatalytic chains [7] etc.

Regardless of the underlying model, we capture the visually evident leader-follower relationship as seen on FIG. 1.

This leads to the following observation: if one effect precedes another, the oriented area on the parametric joint plot of the corresponding functions will surround a positive algebraic area. Of course, the semantics of this assumes that k and l are consubstantial; if their nature is antagonistic, the lead-follow relation flips.

We take this consideration as our primitive on which to build the procedures of data analysis.

Lead Matrix

Let us start with the situation when the trajectory γ is closed.

Consider the iterated integrals:

$$A_{kl} := \tfrac{1}{2} \int \gamma_l d\gamma_k - \gamma_k d\gamma_l. \tag{4}$$

Clearly, these integrals are equal to the oriented areas of the two-dimensional projections of the trajectory on the coordinate planes.

The skew-symmetric matrix A=($A_{kl}$)1≤k,l≤d is called the lead matrix.

An interpretation of the lead matrix coefficients therefore can be that an element $A_{kl}$ is positive if l follows k.

Lead Matrix with Noisy Data

To be able to use the lead matrix in applications, one needs some statistical guarantees of its recoverability from noisy observation, $$\gamma^\epsilon(\tau) = \gamma(\tau) + \epsilon(\tau), \tag{5}$$

where f:C→V is the cyclic observable; R the internal clock parameterization, γ(τ)=f(R(τ)), and ϵ: $\mathbb{R}$ →V the noise.

It should be noted that a naive procedure of taking the sampled lead matrix with coefficients $$(A(\gamma_{a,b}^\epsilon))_{kl} := \tfrac{1}{2} \int_a^b \gamma_k^\epsilon(t) d\gamma_l^\epsilon(t) - \gamma_l^\epsilon(t) d\gamma_k^\epsilon(t) \tag{6}$$

and averaging over time, setting $$\hat{A} := \lim_{t \to \infty} \frac{1}{t} A(\gamma_{0,t}^\epsilon), \tag{7}$$

would fail already for the noise being multidimensional Brownian motion (or some stationary version thereof, like the Ornstein-Uhlenbeck process) for the following reason: the algebraic area of the planar Brownian motion scales as t over the intervals of length t (see, e.g. [6]), adding a nonvanishing error in the limit, and making Â an inconsistent estimator of the lead matrix.

Still, a modification of the procedure can overcome this difficulty. Let $l_1, l_2, l_3, \ldots$ a sequence of the interval lengths, such that $$l_k \to \infty; l_k/L_k \to 0, \text{ as } k \to \infty$$

where $L_k = \Sigma_{j \leq k} l_j$.

:Define the partitioned sampled lead matrices (corresponding to the sequence $l_1, l_2, \ldots$) as $$\bar{A}^\epsilon(k) = \frac{1}{L_k} \sum_{j \leq k} A(\gamma_{L_{j-1}, L_j}^\epsilon), \tag{8}$$

(that is the sum of sampled lead matrices over the consecutive intervals of lengths $l_1, l_2, \ldots$).

We show ([1]) that under the following (rather lax) assumptions the normalized sampled lead matrices converge to the normalized lead matrix over one period, $$\bar{A}^\epsilon(k)/\|\bar{A}^\epsilon(k)\| \to A^P/\|A^P\| \tag{9}$$

This law of large numbers proves the consistency of the partitioned sample lead matrices estimator in our model. We will be using therefore the lead matrices derived from the observed traces as an approximation to actual ones.

Chain of Offsets Model

Consider now the situation where the components of the trajectory γ are quintessentially equivalent processes, with the coordinated internal clocks, but run with a system of offsets. Again, such a system is what one would expect in a process where internally similar subsystems cyclically excite each other.

Model

Such a system would engender a collection of offsets $\alpha_j \in \mathbb{S}^1$, (defined up to a shift). We assume that these processes essentially track the same underlying function, Φ, with, perhaps, some rescaling. That means that $$f_k(t) = a_k \Phi(t - \alpha_k), \quad (10)$$

(in terms of the internal clock), while the (noiseless) trajectory is given by $$\gamma_k(\tau) = a_k \Phi(R(\tau) - \alpha_k), k=1, \ldots, d. \quad (11)$$

From now on we will assume this chain of offsets model (COOM). (The notion of cyclic (non-periodic) processes is of course much broader, and other models may emerge to address situations not adequately described by the COOM.).

For now, the central question we will address, is whether under COOM, one can discover the cyclic order of the functions $f_j$, or, equivalently, the cyclic order of $\alpha_j$, j=1, . . . , d by recovering from the (perhaps, noisy version) of the trajectory, $\gamma^\epsilon$, the sampled lead matrix.

We start by computing the lead matrix over the period under COOM.

Expand the primary function Φ (defined on circle C parameterized by the internal clock T) into the Fourier series, $$\Phi(T) = \sum_k c_k \exp(2\pi i k T) \quad (12)$$

(We emphasize that the periodicity of Φ does not imply any periodicity of the observed γ', as an arbitrary reparametrization of the internal clock acts on Φ on the left.)

The lead matrix over period $(A_{kl}^P) 1 \leq k, l \leq d$ is given by $$A_{kl}^p = 2\pi a_k a_l \sum_{m \geq 1} m|c_m|^2 \sin(m(\alpha_k - \alpha_l)) \quad (13)$$

Recovering the Offsets

Now, given the skew-symmetric matrix A approximating the lead matrix over one period Ap, one might try to reconstruct the cyclic ordering of the offset phases $\alpha_k$'s k=1, . . . , d. We describe here two algorithms for this recovery.

We will rely here on the low rank approximations. A natural simplifying assumption, not infrequent in practice, stipulates that the Fourier expansion (12) is dominated by the leading coefficient: $|c_1|^2$ is much larger that $\Sigma_{|k| \geq 2}|c_k|^2$ (we ignore the constant term, as it is irrelevant to the cyclic behavior).

If φ has just a single harmonic in its expansion, then the skew symmetric matrix $A^P$ would have rank two (spanned by the two rank one matrices, $A^\pm$, with $A_{kl}^+ = \alpha_k \alpha_l \sin(\alpha_k) \cos(\alpha_l)$ and $A_{kl}^- = \alpha_k \alpha_l \cos(\alpha_k) \sin(\alpha_l)$.

In general, even if the function φ has more than one mode, one still can expect, as long as the leading harmonic is dominating φ, that $\overline{A}$ is well approximated (in Frobenius norm) by the rank 2 matrix $P\overline{A}P$, where P is the projection on the 2-plane spanned by the eigenvectors corresponding to the largest in absolute value purely imaginary eigenvalues. Similar stability can be expected for the noisy data, if the sampled lead matrix approximates the one period lead matrix well.

It is immediate that the (complex conjugated) eigenvectors corresponding to the non-vanishing eigenvalues of the rank 2 matrix $A^P$ are given by $$v_1 = e^{i\Psi}(e^{2\pi i \alpha_1}, e^{2\pi i \alpha_2}, \ldots, e^{2\pi i \alpha_1}), v_2 = \overline{v}_1 \text{ (for some phase } \Psi\text{)}.$$

Hence, the spectral decomposition of Ap and the arguments of the components of the first eigenvector would retain the cyclic order of the offsets.

The spectrum of the sampled lead matrix in itself can serve as an indicator of the explanatory power of the cyclicity algorithm. In general, the spectrum of the skew-symmetric lead matrix consists of purely imaginary pairs $\pm i\lambda_j$ and zeros. We reorder the absolute values of the spectral pairs so that, $\lambda_1 \geq \lambda_2 \geq \lambda_3 \geq \lambda_4 \geq \ldots$.

The ratio $\lambda_1/\lambda_3$ indicates how well the lead matrix can be described by the noiseless harmonic model (for which the ratio is $+\infty$).

As a realistic example one can consider the trajectory whose components are iid Brownian bridges (that is Brownian motions starting at the origin and conditioned to end at the origin as well, see [12]). One can show that in the limit of large number of channels d>>1, the ratio is close to 2 [1]. Any data with higher ratio point to rejection of such a hypothesis.

Applying Cyclicity

Artificial Data

To illustrate the power of the approach presented above, we start with noiseless data. We generated J=12 traces of harmonic functions $\sin(t - \alpha_k)$ with random phase offsets (cyclically ordered), and sampled them, at 625 samples per period for 16 periods. The results are shown in FIGS. 2A-2E. We can see the banded, nearly cyclic lead matrix, the spectrum having just two nontrivial (complex conjugate) eigenvalues, and the components of the leading eigenvector close to the circle of radius $1/\sqrt{J}$.

Next, consider a similar example, adding to each of the samples an iid normally distributed values (see FIGS. 3A-3D). In FIGS. 3A-3C, we show the output of quite a noisy sample. As a result, the spectral separation of the leading eigenvalue is far smaller than in the noiseless case; the realigned lead matrix is not so apparently circular and the components of the leading eigenvector do not align on a circle. Still, the cyclic ordering (in this case, the identity permutation) is recovered perfectly with high probability (FIG. 3D).

Analysis of Human Connectome Project Data

Data Description: To test the cyclicity-based approach on the fMRI data we turned to Human Connectome Project, a large consortium of research centers, based at the Washington University in St. Louis, aiming at aggregating high quality annotated data.

In this study, we pulled the fMRI traces of resting subjects. The 200 traces obtained are resting-state fMRI scans available directly from the HCP web site or using the Amazon S3 server[3]. Once downloaded, the nifti files (.nii.gz) can be further processed for use in Matlab using packages available from Mathworks.

The subjects themselves are "healthy adults, ages 22-35, whose race/ethnicity is representative of the US population.[4]

For each of the subjects, the data were then aggregated into 33 voxel groups, Regions of Interest (ROIs), corresponding to anatomically identified regions of the brain, often with a function, or a group of functions correlated with it.

Analysis: For each of the subjects, the full cyclicity analysis was run, yielding a collection of lead matrices (33×33 skew-symmetric matrices); the implied cyclic permutations and vectors of the amplitudes of the components of the leading eigenvalues, serving as a proxy for the signal strength. The predictive power of the leading eigenvector in describing the cyclic structure of the ROIs in the time series can be deduced, heuristically, from the ratio of the absolute value of the leading eigenvalue over the largest of the absolute values of the remaining components: if the reordered absolute values are $|\lambda_1|=|\lambda_2|>|\lambda_3|=|\lambda_4|>\ldots$, then the quality of the ordering defined by the components of $\mu_1$ is $|\lambda_1|/|\lambda_3|$.

Two representative sets of results (out of 200) are shown here. The FIG. 4 shows the results with a high $\lambda_1/\lambda_3$ ratio and, correspondingly, with banded lead matrix after reordering the ROIs according to their phases in the leading eigenvector. The majority of subjects showed a large $\lambda_1/\lambda_3$ ratio.

FIG. 5 shows the cumulative histogram of the ratios $|\lambda_1|/|\lambda_3|$. The data point at the presence of strong signal.

Active regions: Described herein is the existence of some common cyclic process, a consciousness pattern, that can be detected in a large number of the subjects. To this end, we first identify the group of ROIs exhibiting high signal.

A striking pattern of these results was a strong signal of the left primary auditory cortex, while the right primary auditory cortex was hardly showing at all. Other symmetric ROIs with strong signal appeared in pairs. This contrast is clearly indicative of strong asymmetry either in the functionality of the auditory processing (which is rather implausible in the resting state) or of the strong asymmetry in the auditory stimuli during the data collection.

Looking for cyclic patterns: The lead matrix provides an insight into the temporal, cyclic behavior of the interrelated time series. The patterns of cyclic behavior that are observed universally, or which are prevalent in a population are of special interest. To recover these data, we adapt an approach inspired by the Hodge theory paradigm [4].

We were able to recover a collection of ROIs excited in a particular cyclic order in many of the recorded traces. The nuerophysiological significance of this finding is evident. In the recovered cycle, again, the left primary auditory cortex was strongly represented, and the right primary auditory cortex was not.

Functional Biomarkers of Tinnitus Severity using Resting State Functional Connectivity.

We conducted a preliminary resting state study with 12 older adults with tinnitus and high-frequency sensorineural hearing loss (TIN) and two age- and gender-matched control groups: 15 normal hearing adults (NH) and 13 adults with similar hearing loss without tinnitus (HL) (Schmidt et al., 2013). All TIN participants had mild-to-moderate tinnitus as estimated by their scores on the Tinnitus Handicap Inventory (Newman et al., 1996). Five minute long resting-state scans were obtained using a Siemens 3 Tesla Allegra scanner. Data acquisition parameters, data processing, and analysis were as detailed in the "Analysis of fMRI data" section below. A seeding analysis with seeds in the auditory, the dorsal attention (to better parse the effect of frontal and parietal hubs, two sets of seeds were used) and the default mode networks was performed. Details regarding the seed regions are listed in Table 1. Note that the seeds in limbic areas listed in Table 1 were not used in this analysis but will be used in the proposed study.

Results of our analysis revealed a notable relationship between limbic and attention areas in individuals with tinnitus. We identified an increased correlation between the left parahippocampus (emotion processing system) and the auditory network in the TIN group compared to NH controls, as well as an increased correlation between the right parahippocampus and the dorsal attention network in TIN when compared to HL controls. Decreased correlations between the dorsal attention network and other attention-related regions were also observed in the TIN patients when compared to HL controls (FIG. 7). Analysis of the default mode network revealed decreased correlations between seed regions (in the posterior cingulate cortex and medial prefrontal cortex) and the precuneus in TIN patients when compared to both control groups (FIG. 8). This shows that TIN patients have a disrupted default mode network and are not in a true resting state. These results allow for the dissociation of connectivity alterations in the dorsal attention, default mode, limbic and auditory networks resulting from tinnitus and hearing loss from those of hearing loss alone. It also points to potential tinnitus therapies that address the increased engagement of limbic and attention brain regions in resting state networks. In the proposed project, we will extend this work by including participants with a range of tinnitus severity.

TABLE 1

Location of seeds of different networks in MNI (Montreal Neurological Institute) coordinates.

| Network | Seed Region | Coordinates (MNI) Right hemisphere | | | Coordinates (MNI) Left hemisphere | | |
| --- | --- | --- | --- | --- | --- | --- | --- |
| | | X | Y | Z | X | Y | Z |
| Auditory | primary auditory cortex | 55 | −22 | 9 | −41 | −27 | 6 |
| DMN | medial prefrontal cortex | 8 | 59 | 19 | | | |
| DMN | posterior cingulate cortex | | | | −2 | −50 | 25 |
| DAN | posterior intraparietal sulcus | 26 | −62 | 53 | −23 | −70 | 46 |
| DAN | frontal eye field | 27 | −11 | 54 | −25 | −11 | 54 |
| Limbic | amygdala | 18 | −7 | −17 | −17 | −25 | −24 |
| Limbic | parahippocampus | 23 | −21 | −20 | −24 | −22 | −24 |

DMN = Default mode network, DAN = dorsal attention network.

Automated Cluster Analysis of Resting State Data and Associate Subgroups with a Set of Behavioral and Neural Correlates.

Here we develop a method to cluster subjects (using data from the same individuals as in the (Schmidt et al., 2013) study) based on consistent patterns of spatio-temporal dynamics. To exploit the time-dependent patterns of neural activity and in order to enhance clustering capabilities of the tools developed herein, we choose to use a sliding window approach ("Takens' embedding") applied to the traces of subject measurements of specific duration; the data were divided into blocks of either 20, 40, 60 seconds, or taken across the entire scan time (the last served as a control). We abstract the data into a graph in which each voxel is represented as a vertex, while the correlations between these voxels (or vertices) are calculated to serve as weights on the edges of the graph. Physical distance and anatomical structure of the interconnecting tissues between voxels can influence clustering outcomes; to control for this, we rescale the correlations obtained between two voxels by distance, boosting the weights of voxel pairs separated by longer distances. This rescaling takes into account the assumption that correlations that arise from nearby voxels may be artifactual due to reasons other than brain connectivity, such as vasculature. The eigenvector corresponding to the second lowest eigenvalue of the graph Laplacian for this graph was then calculated as is done in preparation for spectral clustering (Shi and Malik, 2000). For each sliding window we obtain one eigenvector for each subject. This collection of eigenvectors is then stacked into one long vector for each subject. We reduce the dimensionality of the data by random projection, a type of data reduction that preserves distance. Clustering is performed on two variations of data: the raw voxel data as is, and the eigenvectors described above. The two preparations are directly compared. Clustering input also varied depending on whether whole brain data were examined, or if only data representing specific regions were examined.

Following this data preparation, we apply k-means clustering and hierarchical clustering (Jain, 2010) using Python software (https://www.python.org/psf). Through variation of the size of the sliding window (20 sec to 60 sec), manipulation of the weighting distance cutoff (10-30 mm), and different clustering techniques (i.e. single-linkage, average-linkage, or Ward's implementation of hierarchical clustering), we obtain various data sub-groupings. Clusters were assessed via the Rand and Silhouette indices. The Rand index (Rand, 1971) assesses true positives and true negatives in a clustering result and ranges from 0 to 1, with 1 being perfect classification. The Silhouette index (Rousseeuw, 1987) measures how well each element in a cluster is classified. In other words, are there other clusters that the elements would fit better in? This measure ranges from −1 to 1 for an element, with 1 indicating appropriate clustering and −1 indicating that an element belongs in a different cluster. We average these individual element scores for an overall Silhouette index value.

In general, hierarchical clustering performed better than k-means clustering. The best hierarchical clustering result was produced using an average linkage method, producing several groupings with a Rand index of 0.8. Silhouette coefficients for the clustering that produced this Rand index were typically around 0.2. In the preliminary analysis, different distance cutoffs did not seem to have a dramatic effect on results. The use of time windows, however, improved clustering accuracy, with a time window of 20 seconds producing clusters with high Rand indices most often. Using higher numbers of clusters also produced better clustering results, with 6 clusters being the most successful.

A sample hierarchical clustering tree is shown in FIG. 9. The tree was created using a distance cutoff of 20 mm, sliding window size of 20 seconds, and an average linkage hierarchical clustering method. In the tree, there are four primary sections, which are marked by black lines in the figure (described left to right): a section of primarily control subjects (left, containing a section of only controls), a section of primarily controls (with three tinnitus subjects), a mixed section of both controls and patients, and a smaller branch of three tinnitus participants. This tree is a representative result of the clustering method applied; in general, there are more control branches, due in part to the larger amount of controls than tinnitus subjects. Interestingly, two of the three left-most tinnitus patients (mixed with control subjects) experienced masking of their tinnitus percept while in the scanner (labeled TIN-M). Because they could not perceive their tinnitus during the scan, they may have exhibited functional connectivity similar to that of a control patient. However, tinnitus patients that did not experience masking were also clustered with controls in a different section, so there may be additional behavioral characteristics driving the classification, such as severity. There could be representations of several tinnitus subgroups within our small subject group. In addition, it is possible that each subgroup drives specific alterations to resting state networks that are being lost by examining whole brain data.

REFERENCES

[1] Yuliy Baryshnikov. Cyclicity and reparametrization-invariant features in time series. Preprint, 2016.

[2] Steven L Bressler and Vinod Menon. Large-scale brain networks in cognition: emerging methods and principles. Trends in cognitive sciences, 14(6):277-290, 2010.

[3] Kuo-Tsai Chen. Integration of paths—a faithful representation of paths by noncommutative formal power series. Transactions of the American Mathematical Society, pages 395-407, 1958.

[4] Jozef Dodziuk. Finite-difference approach to the hodge theory of harmonic forms. American Journal of Mathematics, 98(1):79-104, 1976.

[5] Giovanni Dosi, Giorgio Fagiolo, and Andrea Roventini. An evolutionary model of endogenous business cycles. Computational Economics, 27(1):3-34, 2006.

[6] B Duplantier. Areas of planar brownian curves. Journal of Physics A: Mathematical and General, 22(15):3033, 1989.

[7] Manfred Eigen and Peter Schuster. A principle of natural selforganization. Naturwissenschaften, 64(11):541-565, 1977.

[8] Michael D Fox and Marcus E Raichle. Spontaneous fluctuations in brain activity observed with functional magnetic resonance imaging. Nature Reviews Neuroscience, 8(9):700-711, 2007.

[9] Karl J Friston. Functional and effective connectivity: a review. Brain connectivity, 1(1):13-36, 2011.

[10] R Matthew Hutchison, ThiloWomelsdorf, Elena A Allen, Peter A Bandettini, Vince D Calhoun, Maurizio Corbetta, Stefania Della Penna, Jeff H Duyn, Gary H Glover, Javier Gonzalez-Castillo, et al. Dynamic functional connectivity: promise, issues, and interpretations. Neuroimage, 80:360-378, 2013.

[11] Ruwan D Ranaweera, Minseok Kwon, Shuowen Hu, Gregory G Tamer, Wen-Ming Luh, and Thomas M Talavage. Temporal pattern of acoustic imaging noise asymmetrically modulates activation in the auditory cortex. Hearing research, 331:57-68, 2016.

[12] Daniel Revuz and Marc Yor. Continuous martingales and Brownian motion, volume 293. Springer Science & Business Media, 2013.

[13] Peter Turchin, Lauri Oksanen, Per Ekerholm, Tarja Oksanen, and Heikki Henttonen. Are lemmings prey or predators? Nature, 405(6786):562-565, 2000.

[14] Martijn P Van Den Heuvel and Hilleke E Hulshoff Pol. Exploring the brain network: a review on resting-state fmri functional connectivity. European Neuropsychopharmacology, 20(8):519-534, 2010.

Example 2

Dissociating Tinnitus Patients from Healthy Controls Using Resting-State Cyclicity Analysis and Clustering Abstract Chronic tinnitus is a common and sometimes debilitating condition that lacks scientific consensus on physiological models of how the condition arises as well as any known cure. In this study, we applied a novel cyclicity analysis, which studies patterns of leader-follower relationships between two signals, to resting-state functional magnetic resonance imaging (rs-fMRI) data of brain regions acquired from subjects with and without tinnitus. Using the output from the cyclicity analysis, we were able to differentiate between these two groups with 58-67% accuracy by using a partial least squares discriminant analysis. Stability testing yielded a 70% classification accuracy for identifying individual subjects' data across sessions 1 week apart. Additional analysis revealed that the pairs of brain regions that contributed most to the dissociation between tinnitus and controls were those connected to the amygdala. In the controls, there were consistent temporal patterns across frontal, parietal, and limbic regions and amygdalar activity, whereas in tinnitus subjects, this pattern was much more variable. Our findings demonstrate a proof-of-principle for the use of cyclicity analysis of rs-fMRI data to better understand functional brain connectivity and to use it as a tool for the differentiation of patients and controls who may differ on specific traits.

SUMMARY

Chronic tinnitus is a common, yet poorly understood, condition without a known cure. Understanding differences in the functioning of brains of tinnitus patients and controls may lead to better knowledge regarding the physiology of the condition and to subsequent treatments. There are many ways to characterize relationships between neural activity in different parts of the brain. Here, we apply a novel method, called cyclicity analysis, to functional MRI data obtained from tinnitus patients and controls over a period of wakeful rest. Cyclicity analysis lends itself to interpretation as analysis of temporal orderings between elements of time-series data; it is distinct from methods like periodicity analysis or time correlation analysis in that its theoretical underpinnings are invariant to changes in time scales of the generative process. In this proof-of-concept study, we use the feature generated from the cyclicity analysis of the fMRI data to investigate group level differences between tinnitus patients and controls. Our findings indicate that temporal ordering of regional brain activation is much more consistent in the control population than in tinnitus population. We also apply methods of classification from machine learning to differentiate between the two populations with moderate amount of success.

Introduction

Chronic subjective tinnitus, the long-term perception of a sound with no external source, is a relatively common hearing disorder affecting 4-15% of the population (Møller, 2007). A portion of these individuals are extremely distressed by the percept, which exerts a significant debilitating effect on their lives. However, the diagnosis of tinnitus and the assessment of tinnitus distress are typically made through self-report questionnaires, and a consensus regarding psychophysiological models of tinnitus is lacking. Part of the reason for impaired progress in developing an understanding of the biology of the disorder has been the discrepant and often contradictory evidence in the neuroscientific literature. An improved understanding of the neural underpinnings of tinnitus would benefit both diagnosis of the disorder as well as the generation of therapies and perhaps the predictability of a therapy's effectiveness at an individual level.

Tinnitus is a highly heterogeneous condition in terms of etiology, laterality of the percept, type of sound (e.g., tonal, modulating, broad-band), pitch, loudness, age, and nature of onset, duration, and severity. This heterogeneity has made the condition difficult to study using structural (sMRI) and functional magnetic resonance imaging (fMRI), because MRI studies typically include relatively small sample sizes (see Friston, Holmes, & Worsley, 1999). Controlling for all the variables that may contribute to the neural underpinnings of tinnitus is therefore a difficult statistical challenge, as is interpreting differences between samples with diverse parameters for subject recruitment. The brain regions implicated in tinnitus commonly differ across studies, which may be due in part to the heterogeneity of the condition. It remains unclear whether functional differences are capable of reliably distinguishing tinnitus patients from normal controls, or distinguishing subgroups of patients with tinnitus.

Tinnitus-related brain differences have been observed across many applications of MRI, including anatomical analysis, task-based functional imaging, and resting-state functional connectivity (rs-FC) analyses (Adjamian, Sereda, & Hall, 2009; Allan et al., 2016; Husain, 2016; Husain & Schmidt, 2014). Rs-FC analysis finds interregional correlations of spontaneous brain activity, which reliably organizes into coherent resting-state networks (RSNs) (Fox et al., 2005; Mantini, Perrucci, Del Gratta, Romani, & Corbetta, 2007; Raichle & Snyder, 2007; Shulman et al., 1997). Rs-FC is an interesting candidate to examine for a significant neural change accompanying a disorder because communication between brain regions may be altered in the absence of large morphological changes. In addition, in the normal population, replicability of rs-FC is high (Shehzad et al., 2009). The replicability is comparable to task-based fMRI (Mannfolk et al., 2011), but unlike task-based fMRI, the experimenter may be less concerned that an experiment failed because of poor experimental design, since there is no task. In fact, rs-FC has been shown to be altered across a number of neuropsychological conditions (Barkhof, Haller, & Rombouts, 2014), and there is recent evidence that Rs-FC is also altered in tinnitus (Husain & Schmidt, 2014). Rs-FC is also relevant in tinnitus because those with the chronic condition are presumably aware of their internal sound while being scanned, whereas the control groups do not have such an internal sound to which they can attend.

However, it is possible that the general correlations between regions of the brain do not drastically change within tinnitus, but rather that some dynamic, time-varying relationship between regions would be more sensitive to the disorder. Rather than depending on static correlations between regions over an entire time course of the resting-state task, we considered manipulating the temporal qualities of the resting-state data to look for time-dependent patterns of activity between regions.

Many classical mathematical and statistical tools have been useful in analyzing signals, which are periodic in time or which seek to identify time-varying correlations between multiple signals. However, the signal may also be cyclic, but aperiodic, where there may be a consistent temporal ordering between signals without a predictable period between cycles. Fluctuations in the brain's functional topology has been an emerging and important area of study within cognitive neuroscience (H. Chen et al., 2013). An analysis of cyclic relationships between brain regions would therefore be useful to examine the possibility of consistent temporal ordering of the spontaneous activity of certain brain regions—a so called "leader-follower" structure. This lead matrix provides the strength of the temporal ordering between pairs of regions of interest (ROIs) included in the analysis. Looking at differences in this leader-follower structure between groups may reveal important insights into understanding changes in global functional organization, and may subsequently help in the classification between members of these groups. To this end, we employed a recently developed cyclicity analysis method (Baryshnikov & Schlafly, 2016) on a set of tinnitus patients (TIN) and normal hearing controls (NH) to determine whether the cyclic relationships between brain regions has the potential to help distinguish these two groups.

Cyclic signal: A cyclic signal is one that repeats itself identically over and over again but perhaps with a variable speed. Periodic signals are cyclic while converse is not true.

Described herein, cyclicity analysis is performed on a subset of resting-state fMRI data acquired to better understand neural mechanisms of tinnitus. Multiple methods of classification are explored after dimension reduction. These methods include quadratic and linear support vector machines (SVM), linear and quadratic discriminant analysis (DA), and partial least squares discriminant analysis (PLS-DA). Because cyclicity is a novel way to analyze fMRI data, many characteristics of the cyclicity analysis are additionally explored.

Results
Cyclicity Analysis

The cyclicity analysis was performed on the time-series data from 33 ROIs for each subject, generating a lead matrix where each element of the matrix corresponds to the temporal ordering between two ROIs. The magnitude of the cyclic signal from an ROI can be analyzed by examining the leading eigenvalue and corresponding eigenvector of a subject's lead matrix. A larger modulus of an element of that eigenvector translates into a larger signal corresponding to the ROI associated with that element. Greater magnitude cyclic signals here may be interpreted as a more constrained temporal ordering. The cyclicity analysis provides a cyclic ordering of ROIs, but the direction of the cycle cannot be determined. Therefore, the strength of the ordering, rather than the direction, is the focus of the analysis. The magnitude of the cyclic signals from each ROI were computed separately for both the controls and the tinnitus groups as in FIG. 10. It was found that left and right cuneus corresponded to the greatest magnitude signals in both groups of subjects.

Principal component analysis (PCA) was performed, and it was found further that the primary contributor to the direction of greatest variation in both test groups also corresponded to the left and right cuneus. This can be visualized in the matrix generated from the first component loading vector from the PCA analysis (FIGS. 11A-11B). The loading vector consists of coefficients in the linear combination of original variables that generate principal component scores. These findings together were interpreted to mean that the cuneus ROIs did not contribute any discriminatory information between the two groups. Therefore, these ROIs were removed from further analysis.

Phase magnitudes: Each complex entry of an eigenvector of the lead matrix corresponds to an ROI. The phase magnitudes associated with an eigenvalue $\lambda$ for each ROI are the absolute values of these entries Difference of First Principal Components Between Groups The covariance structure of the data for each group was studied separately after removing the left and right cuneus from the time course data. PCA was used to achieve dimension reduction prior to classification. FIGS. 12A-12B show the first and second loading vectors (i.e., those that account for the most variance in the data) for the tinnitus and normal hearing controls. The first and second components appear to switch between the two groups. In the normal hearing controls, the first component is weighted toward the cyclic relationships with the primary visual cortices and occipital lobe, while the second component is more weighted toward the precuneus and amygdala. In contrast, in the tinnitus group, the first component seems to be strongly weighted toward the cyclic connectivity of the precuneus while the amygdala is less constrained, and the second component seems to be weighted toward the visual areas.

Stability Analysis

The results of a k-nearest neighbor (k-NN) analysis for the subject classification across sessions is presented in FIG. 13. In FIG. 13, the row designates the subject. The goal of this analysis was to see if we could create a training set, based on the cyclicity analysis of data separated by 1 week from the testing set, and accurately predict if the cyclicity data from one run belonged to a specific subject. Perfect classification would mean that all the subjects were classified correctly four times (each run was classified correctly), and would look like uniform brightness down the diagonal of the figure. We found a 70% accuracy for classifying the runs, with 21 out of the 47 subjects being classified perfectly, signaling that the lead matrix is a viable candidate as a feature to use for classification.

Traditional Classification

Four classification methods, linear SVM and DA, as well as quadratic SVM and DA methods were attempted after using PCA for dimension reduction to 10 features. To avoid overfitting or the curse of dimensionality only reduction up to 10 dimensions were tried for these methods. We also attempted PLS-DA using 20 latent components. The confusion matrices and accuracies from these analyses are shown in Table 2.

TABLE 2

Classification Results

| | Controls | Tinnitus |
|---|---|---|
| Linear SVM | | |
| Controls | 26.73% | 73.27% |
| Tinnitus | 19.38% | 80.63% |
| | | Accuracy: 63.43% |
| Linear Discriminant | | |
| Controls | 31.13% | 68.87% |
| Tinnitus | 20.75% | 79.25% |
| | | Accuracy: 63.89% |
| Quadratic SVM | | |
| Controls | 30.73% | 69.27% |
| Tinnitus | 27.00% | 73.00% |
| | | Accuracy: 59.51% |
| Quadratic discriminant | | |
| Controls | 15.87% | 84.13% |
| Tinnitus | 21.97% | 78.03% |
| | | Accuracy: 58.81% |

TABLE 2-continued

Classification Results

| | Controls | Tinnitus |
|---|---|---|
| | PLS-DA | |
| Controls | 32.45% | 67.55% |
| Tinnitus | 28.29% | 71.71% |
| | | Accuracy: 59.03% |

Note:
(Rows represent the true class and columns represent the predicted class.)

Because there was a greater number of tinnitus subjects in our sample than control subjects, we were interested in examining the same classification procedures after randomly selecting members from the tinnitus group to match the size of the normal hearing group before training a classifier. The results of this analysis are shown in Table 3.

TABLE 3

Classification results with equal class sizes

| | Controls | Tinnitus |
|---|---|---|
| | Linear SVM | |
| Controls | 56.67% | 43.33% |
| Tinnitus | 42.93% | 57.07% |
| | | Accuracy: 56.87% |
| | Linear discriminant | |
| Controls | 56.47% | 43.53% |
| Tinnitus | 44.60% | 55.40% |
| | | Accuracy: 55.93% |
| | Quadratic SVM | |
| Controls | 54.20% | 45.80% |
| Tinnitus | 45.13% | 54.87% |
| | | Accuracy: 54.53% |
| | Quadratic discriminant | |
| Controls | 51.60% | 48.40% |
| Tinnitus | 48.47% | 51.53% |
| | | Accuracy: 51.57% |
| | PLS-DA | |
| Controls | 58.09% | 41.91% |
| Tinnitus | 40.77% | 59.23% |
| | | Accuracy: 58.60% |

Note:
(Rows represent the true class and columns represent the predicted class.)

Wilks' Lambda for Variable Selection

The Wilks' criterion was used to select variables, that is, elements of the lead matrices that were most discriminatory across the whole dataset. We selected the 20 most discriminating ROI pairs to use to reduce the dimensions of data in our training set instead of PCA. The classification results obtained by using data from only the top 20 most discriminating ROI pairs is presented in Table 4.

TABLE 4

Classification results using top 20 most discriminating ROI pairs.

| | Controls | Tinnitus |
|---|---|---|
| | Linear SVM | |
| Controls | 23.53% | 76.47% |
| Tinnitus | 17.25% | 82.75% |
| | | Accuracy: 63.85% |

TABLE 4-continued

Classification results using top 20 most discriminating ROI pairs.

| | Controls | Tinnitus |
|---|---|---|
| | Linear discriminant | |
| Controls | 34.07% | 65.93% |
| Tinnitus | 29.00% | 71.00% |
| | | Accuracy: 59.21% |
| | Quadratic SVM | |
| Controls | 32.93% | 67.07% |
| Tinnitus | 24.44% | 75.56% |
| | | Accuracy: 61.96% |
| | Quadratic discriminant | |
| Controls | 7.13% | 92.87% |
| Tinnitus | 7.81% | 92.19% |
| | | Accuracy: 65.04% |
| | PLS-DA | |
| Controls | 52.47% | 47.53% |
| Tinnitus | 31.31% | 68.69% |
| | | Accuracy: 63.51% |

Note:
(Rows represent the true class and columns represent the predicted class.)

Wilks' lambda: A measure of discriminatory ability of a variable, $$\Lambda = \frac{|A|}{|A+B|}$$

where A is the within group sum of squares and cross products matrix (SSCP), B is the between group SSCP matrix and |·| denotes determinant.

Cosine Metric: A measure of similarity, $1-\cos\theta$, between real valued finite dimensional vectors u, v, defined using the dot product $u \cdot v = |u| \, |v| \cos\theta$, where $|u|$ is the Euclidean norm on u. It is zero if and only if one vector is a positive multiple of the other; it is not a true metric.

Because some of these features were likely to be particularly discriminating in only this sample, it was of interest to further examine the stability of the ROI pairs selected by using the Wilks' criterion. This was done by randomly selecting 1,000 subsets of the data and running Wilks analysis. The subset of ROI pairs that consistently showed up across a range of subsets is shown in FIG. 14. We chose the top 10 most stable ROI pairs from this analysis to use for subsequent classification in order to compare with the results from the top 20 most discriminating ROI pairs (Table 5).

TABLE 5

Classification results using top 10 most discriminating ROI pairs.

| | Controls | Tinnitus |
|---|---|---|
| | Linear SVM | |
| Controls | 20.47% | 79.53% |
| Tinnitus | 11.25% | 88.75% |
| | | Accuracy: 66.96% |
| | Linear discriminant | |
| Controls | 30.73% | 69.27% |
| Tinnitus | 19.16% | 80.84% |
| | | Accuracy: 64.85% |

TABLE 5-continued

Classification results using top 10 most discriminating ROI pairs.

|  | Controls | Tinnitus |
| --- | --- | --- |
|  | Quadratic SVM | |
| Controls | 31.73% | 68.27% |
| Tinnitus | 24.72% | 75.28% |
|  |  | Accuracy: 61.38% |
|  | Quadratic discriminant | |
| Controls | 23.60% | 76.40% |
| Tinnitus | 27.91% | 72.09% |
|  |  | Accuracy: 56.62% |
|  | PLS-DA | |
| Controls | 50.47% | 49.53% |
| Tinnitus | 25.20% | 74.80% |
|  |  | Accuracy: 67.03% |

Note:
(Rows represent the true class and columns represent the predicted class.)

Examination of Elements Identified Through Wilks' Lambda

The lambda values correspond to elements of the lead matrix, and thus to ROI pairs. The top 20 discriminatory ROI pairs are graphically presented in FIG. 16 and FIG. 17. These ROI pairs represent the leader-follower relationships that are the most useful out of the whole lead matrix for discriminating between patients with tinnitus and controls and therefore are useful for understanding the underlying relevant cyclic functional connectivity. FIG. 16 shows the flow graph where activity follows downwards and line thickness is indicative of the consistency of the relationships. It is possible to see that the normal hearing controls have much more consistent relationships, especially in regard to the activity preceding amygdalar activity. FIG. 17 focuses on the graph edges where the leader-follower relationship switches direction as a function of group membership. A graphical representation of the location and networks of these ROI pairs are depicted in FIG. 15.

Discussion

As described herein, we have demonstrated the ability of a novel cyclicity analysis applied to resting-state functional MRI data to classify tinnitus patients and normal hearing controls. This approach not only provides a new tool the may be useful for discriminating between groups of subjects, but also provides information about the neural functional connectivity that is most helpful for discriminating between those groups The broadest finding, that patterns of cyclic ordering in resting-state data are helpful for classifying various groups, warrants further investigation. It has been unclear whether networks of correlated neural activity across the brain have any underlying cyclic patterns where one network or region within a network consistently precedes the activity in other networks or regions. See Keilholz (2014) for an interesting review and perspective of this question and a discussion of quasiperiodic patterns in brain activity, and Mitra, Snyder, Blazey, and Raichle (2015) for the recent demonstration of temporal sequences of propagated activity through the brain. The method used here adds to this work by incorporating a new tool capable of analyzing ordered patterns of activity that are aperiodic and vary over time. In our data, subjects showed reliable patterns of variability in their lead matrix across fMRI runs, which demonstrates the potential to analyze aspects of the cyclic signal in order to pull out subject-specific trait information. Our findings suggest that there are differential strengths of the resting signals across ROIs and differences in the consistency of the leader-follower relationships between ROI pairs. For example, in our data, the bilateral cuneus had the strongest signal in the resting-state data. However, despite the strength of the signal in these regions, it appeared that the contribution of the bi-lateral cuneus was similar in both the normal hearing and tinnitus groups, and was therefore likely overwhelming signals from other ROIs that were more useful in predicting the control group from the tinnitus patients.

This may explain some of the poorer performance of the classification after dimension reduction through PCA. Much of the variation in each group's respective lead matrix may be similar and therefore would not likely lead to good discrimination between the two groups, especially when the most consistent orderings between ROI pairs dominate the lead matrix. This may be particularly problematic for a heterogeneous condition like tinnitus, which may cause more variability in brain activity and less consistent orderings between ROI pairs. Our classification identified most of the subjects' data as "tinnitus," so even though there was relatively high sensitivity for identifying tinnitus through the brain data, there was very low specificity. This bias toward classifying subjects as tinnitus was ameliorated after randomly reducing the size of the tinnitus training set to the size of the control training set, although it decreased the accuracy of the classification.

Partial least squares regression more directly analyzes the relationships between the elements of the lead matrix and the group labels (tinnitus and control). This method is therefore advantageous for discrimination because the training set is not blind to the group label in the generation of latent variables for the DA.

Another approach is to choose specific ROI pairs for further analysis as an alternative to dimension reduction through the generation of latent variables or principal components. We can use the Wilks lambda criterion to examine which ROI pairs are the most useful for discriminating between the two groups and choose a subset of those ROI pairs for further analysis.

This added benefit is useful for examining the patterns of neural activity that have some bearing on the discrimination between tinnitus patients and normal hearing subjects. In our data, we chose to use the top 20 ROI pairs given by Wilks' lambda criterion. None of the ROI pairs by themselves has an exceptional Wilks' lambda, but together, these 20 ROI pairs lead to better classification. The improved classification by using lambda values derived from the entire dataset to select ROI pairs for further analysis is partially due to the inherent double dipping of the data in this approach. To try to lessen the impact of double dipping in the classification, a subset of ROI pairs was selected that consistently appeared in the top 20 most discriminating lambda values when analyzing subsets of the data.

The analysis of the differences in the 20 best discriminating ROI pairs between the two groups yields the best evidence to help understand changes in neural activity that contribute to chronic tinnitus. Looking at this data, the clearest discriminating pattern of activity is that the cyclic connectivity with the amygdala is important in distinguishing tinnitus patients from controls. This result is strongly predicted from the extant literature. A review of the literature by Simonetti & Oiticica (2015) emphasizes the broad changes in neural activity across the brain in tinnitus depending on the paradigm used to study the condition. In addition, the data presented here suggests that the ordering between the amygdala and other ROIs is less constrained and more heterogeneous than that of the normal hearing controls. Davies, Gander, and Hall (2017) recently reported reduced amygdalar activity to emotionally evocative sound clips in tinnitus patients compared with controls. The heterogeneity in this region may result from differences in levels of habituation to tinnitus. Some tinnitus patients may have reduced amygdala activation following habituation, whereas others may have increased amygdala activation to the bothersome internal noise. Many nonauditory areas of the brain have been implicated in tinnitus, especially in fronto-parietal and limbic regions. Recently, Carpenter-Thompson, Schmidt, McAuley, and Husain (2015) investigated differences specifically between subgroups of patients exhibiting high distress and low distress from the condition, and found that the high distress group recruited the amygdala and parahippocampus to a greater extent in an affective sound listening task.

Changes in amgydalar activity is largely consistent with both the literature on tinnitus as well as in other conditions with some contribution of emotional dysfunction, such as depression. In depression, there is heightened amygdala responses to emotional stimuli (Sheline et al., 2001), but at the same time there is reduced connectivity between the amygdala and the affective network (Veer et al., 2010). The observed changes in cyclic connectivity may contribute to cognitive deficits in attention that have been seen in tinnitus (Trevis, McLachlan, & Wilson, 2016) and may affect the overall patterns of network connectivity that change in tinnitus (Schmidt, Akrofi, Carpenter-Thompson, & Husain, 2013; Schmidt, Carpenter-Thompson, & Husain, 2017). A loss of connectivity may also correspond with the less constrained pattern of leader-follower relationships involving the amygdala, and future research should seek to better understand this correspondence.

The classification itself is an important contribution of this work. This study serves as a proof-of-concept for the usefulness of cyclicity analysis in classifying a group of tinnitus patients from controls. The classification presented here is promising, especially for having been completed on a somewhat small sample of tinnitus patients and normal controls. Neural correlates of tinnitus would be useful for future predictions about the underlying causes of the condition, as well as leading to an objective diagnostic tool that may be validating for patients and helpful for clinicians. However, there are limits to the classification here that are evident in our analysis. First, the classification would likely benefit from a larger control group to match the sample size of the tinnitus group. Secondly, the classification after selecting ROI pairs with Wilks' lambda is promising.

A larger sample size may improve classification, and compare the classification from the cyclicity analysis of resting state fMRI data to the classification from more traditional dynamic and static functional connectivity analyses. In addition, these parameters, along with behavioral and anatomical characteristics, should be combined to see if additional features contribute to even greater classification accuracy. Finally, future work will compare tinnitus patients with controls who have matched hearing loss. This is important because hearing loss often accompanies tinnitus, and it is critical that the condition of tinnitus be discriminable from other coexisting conditions. In the data presented here, most control participants have normal hearing, while the tinnitus patients do not; the differences in cyclicity patterns and promising classification could therefore be related to the differences in hearing thresholds. Alternatively, accounting for hearing loss may further improve classification.

Conclusion

The provided results demonstrate that normal hearing controls and tinnitus patients can be classified through cyclicity analysis of resting-state fMRI data. Based on discriminative features (in this case, the leader-follower relationships of ROI pairs), a classification model can be built to predict if an individual has chronic tinnitus. These discriminative ROI pairs can also be used to characterize the nature of differences in brain activity between normal hearing controls and tinnitus patients, which may lead to better diagnostic tools and an improved understanding of the neural underpinnings of tinnitus. This method may combine this cyclicity analysis with other forms of potentially discriminating data to make improved classifications of tinnitus subjects from controls.

Materials and Methods

Participants

Participants were recruited from the Champaign-Urbana area as part of a larger ongoing study with community advertisements in flyers, bulletins, and newspapers. Study approval was obtained from the University of Illinois at Urbana-Champaign and written informed consent was obtained from each participant (UIUC IRB protocol no. 15955). fMRI data were collected from two groups of participants: 15 controls with no tinnitus (mean age 46.27±11.71, 10 women) and 32 patients with chronic tinnitus (mean age 51.16±10.73, 14 women). Demographic details are provided in Table 6.

TABLE 6

Demographics for subject groups (Significant at the p < .05 level. Scores from Becks Depression Inventory, Beck Anxiety Inventory, and the Tinnitus Functional Index were acquired at each imaging session and averaged together. Means (M) and standard deviations (SD) are presented for each group, and p values associated with two-sample t tests between group means are displayed. Pure tone averages at 250, 500, 1,000, 2,000, 3,000, 4,000, 6,000, 8,000, 9,000, 10,000, 11,200, 12,500, 14,000, and 16,000 Hz are presented for both right and left ears).

|  | Controls (N = 15, 10 female) | | Tinnitus (N = 32, 14 female) | | |
| --- | --- | --- | --- | --- | --- |
|  | M | SD | M | SD | p-value |
| Age | 46.27 | 11.71 | 53.16 | 10.73 | 0.05 |
| Beck's Depression Inventory | 3.07 | 6.37 | 4.63 | 5.52 | 0.39 |
| Beck Anxiety Inventory | 1.59 | 1.91 | 2.69 | 3.77 | 0.30 |

TABLE 6-continued

Demographics for subject groups (Significant at the p < .05 level. Scores from Becks Depression Inventory, Beck Anxiety Inventory, and the Tinnitus Functional Index were acquired at each imaging session and averaged together. Means (M) and standard deviations (SD) are presented for each group, and p values associated with two-sample t tests between group means are displayed. Pure tone averages at 250, 500, 1,000, 2,000, 3,000, 4,000, 6,000, 8,000, 9,000, 10,000, 11,200, 12,500, 14,000, and 16,000 Hz are presented for both right and left ears).

|  | Controls (N = 15, 10 female) | | Tinnitus (N = 32, 14 female) | | |
| --- | --- | --- | --- | --- | --- |
|  | M | SD | M | SD | p-value |
| Tinnitus Functional Index | | | | | |
| Total | N/A | N/A | 23.44 | 17.78 | N/A |
| Intrusive | N/A | N/A | 39.43 | 20.46 | N/A |
| Sense of control | N/A | N/A | 36.77 | 23.01 | N/A |
| Cognitive | N/A | N/A | 22.29 | 19.62 | N/A |
| Sleep | N/A | N/A | 15.99 | 21.36 | N/A |
| Auditory | N/A | N/A | 25.89 | 27.13 | N/A |
| Relaxation | N/A | N/A | 26.51 | 24.27 | N/A |
| Quality of life | N/A | N/A | 13.87 | 18.31 | N/A |
| Emotional | N/A | N/A | 9.95 | 10.49 | N/A |
| Pure tone averages | | | | | |
| Right 250 Hz | 12.00 | 10.14 | 13.28 | 6.04 | 0.59 |
| Right 500 Hz | 10.67 | 5.31 | 12.81 | 6.95 | 0.30 |
| Right 1000 Hz | 11.33 | 8.12 | 12.34 | 4.40 | 0.58 |
| Right 2000 Hz | 12.00 | 7.51 | 17.81 | 10.31 | 0.06 |
| Right 3000 Hz | 13.67 | 11.41 | 24.22 | 17.37 | 0.04* |
| Right 4000 Hz | 16.00 | 16.50 | 27.03 | 18.62 | 0.06 |
| Right 6000 Hz | 16.67 | 19.24 | 30.78 | 19.06 | 0.02* |
| Right 8000 Hz | 15.67 | 22.75 | 30.47 | 20.96 | 0.03* |
| Right 9000 Hz | 21.00 | 19.29 | 38.75 | 21.96 | 0.01* |
| Right 10000 Hz | 21.67 | 22.57 | 41.09 | 22.78 | 0.01* |
| Right 11200 Hz | 30.00 | 25.64 | 47.50 | 21.02 | 0.02* |
| Right 12500 Hz | 38.33 | 26.70 | 56.88 | 19.58 | 0.01* |
| Right 14000 Hz | 45.33 | 28.19 | 64.22 | 15.35 | 0.00* |
| Right 16000 Hz | 44.00 | 16.39 | 49.84 | 13.94 | 0.21 |
| Left 250 Hz | 9.00 | 7.37 | 15.00 | 12.25 | 0.09 |
| Left 500 Hz | 10.00 | 5.35 | 13.75 | 10.78 | 0.21 |
| Left 1,000 Hz | 10.00 | 6.55 | 12.50 | 9.67 | 0.37 |
| Left 2,000 Hz | 12.00 | 8.41 | 18.59 | 11.59 | 0.06 |
| Left 3,000 Hz | 15.00 | 12.54 | 27.19 | 16.51 | 0.01* |
| Left 4,000 Hz | 17.33 | 18.89 | 29.22 | 17.19 | 0.04* |
| Left 6,000 Hz | 17.67 | 17.51 | 34.38 | 18.65 | 0.01* |
| Left 8,000 Hz | 14.67 | 16.31 | 33.44 | 21.27 | 0.00* |
| Left 9,000 Hz | 17.33 | 15.45 | 43.44 | 22.23 | 0.00* |
| Left 10,000 Hz | 19.67 | 15.86 | 47.03 | 22.93 | 0.00* |
| Left 11,200 Hz | 25.33 | 22.08 | 52.81 | 23.21 | 0.00* |
| Left 12,500 Hz | 37.67 | 27.31 | 60.63 | 23.38 | 0.00* |
| Left 14,000 Hz | 46.00 | 29.95 | 63.75 | 18.14 | 0.02* |
| Left 16,000 Hz | 41.00 | 20.02 | 50.63 | 14.85 | 0.07 |

Imaging

The steps involved in the imaging data analysis are described visually in FIG. 18.

Data Acquisition

All imaging data were collected using a 3T Siemens Magnetom Prisma MRI scanner. A high-resolution, T1-weighted sagittal MPRAGE image (TR=2,300 ms, TE=2.32 ms, flip angle=89°, 192 slices, voxel size=0.9 0.9 0.9 mm3) and a lower-resolution, T2-weighted, image (TR=3400 ms, TE=65 ms, flip angle=120°, 38 slices, voxel size=1.2 1.2 3.0 mm3) were both collected for use during preprocessing. Resting-state data was collected at two sessions, 1 week apart. Two 10-min runs of resting-state data were acquired at both sessions. Resting-state BOLD acquisition used a gradient echo-planar EPI sequence with transversal orientation (TR=2,000 ms, TE=25 ms, flip angle=90°, 38 slices, voxel size=2.5 2.5 3.0 mm3). During the resting-state scans, participants were instructed to lie still with eyes open fixated on a cross presented to them, and to not think about anything in particular. The first four volumes of each run were discarded prior to preprocessing to allow for magnet stabilization. Thus, of the 304 volumes collected in each run (four runs were collected per subject), 300 were used for subsequent analysis.

Resting-State Preprocessing

Preprocessing was performed using SPM12 (Wellcome Trust Centre for Neuroimaging, http://www.fil.ion.u-cl.ac.uk/spm/software/spm12/). Slice-time correction was first applied to the interleaved, ascending data. Functional images were realigned according to a six-parameter rigid body transformation to correct for head motion. Seven subjects were removed from subsequent analysis due to motion exceeding a 2-mm translation or 2° rotation in one of the resting-state runs. Following this, two coregistration steps were performed. First, the T2-weighted image was registered to the mean functional image generated during realignment. Second, the MPRAGE image was registered to the resulting T2-weighted image. Next, the MPRAGE image was normalized to MNI space via a nonlinear warp transformation. The resulting image was used to normalize the realigned functional data. Lastly, the functional images were smoothed using a Gaussian kernel of 8×8×8 mm3 full width at half-maximum.

Regions of Interest Preparation

With the preprocessing steps completed, the resulting image files were converted into matrices to extract time courses within an ROI. From the full brain data, we selected ROIs in the brain that were to be representative of resting-state networks that have been shown to be altered in tinnitus patients. A list of ROIs, including the networks they represent, is included in Table 7. To account for the variability of location of the ROIs different subjects, we averaged the fMRI data in a region of radius 8 mm about the point listed in Table 7, using the MARSBAR toolbox in SPM (Brett, Anton, Valabregue, & Poline, 2002) to define the ROI coordinates. We chose to focus on four main networks comprising of 33 ROIs for this analysis, which have been previously implicated as differing in patients with tinnitus (Burton et al., 2012; Husain & Schmidt, 2014; Maudoux et al., 2012a, 2012b; Schmidt et al., 2013, 2017; Wineland, Burton, & Piccirillo, 2012): the default mode network, the dorsal attention network, the auditory network and limbic regions. The ROI extraction resulted in a 33×300 matrix as a time course per subject.

TABLE 7

Regions-of-interest used in cyclicity analysis

| Name | Center coordinates | Network |
|---|---|---|
| L amygdala | −17, −2, −24 | Limbic |
| L anterior insula | −36, 3, 7 | Attention control |
| L cuneus | −4, −88, 16 | Visual |
| L frontal eye field | −25, −11, 54 | Dorsal attention |
| L inferior frontal lobe | −41, 6, 10 | Attention control |
| L inferior parietal lobe | −31, 68, 32 | Default mode |
| L mid frontal gyrus | −39, 11, 38 | Attention control |
| L parahippocampus | −24, −22, −24 | Limbic |
| L posterior intraparietal sulcus | 26, −62, 53 | Dorsal attention |
| L primary auditory cortex | 55, −27, 9 | Auditory |
| L primary visual cortex | −11, −84, 1 | Visual |
| L superior occipital lobe | −12, −80, 23 | Visual |
| L superior temporal junction | −49, −53, 28 | Ventral attention |
| L superior temporal sulcus | −56, −52, 9 | Ventral attention |
| L ventral intraparietal sulcus | −30, −83, 13 | Dorsal attention |
| Medial prefrontal cortex | 8, 59, 19 | Default mode |
| Posterior cingulate cortex | −2, −50, 25 | Default mode |
| Precuneus | 0, −56, 50 | Default mode |
| R amygdala | 18, −7, −17 | Limbic |
| R anterior insula | 36, 3, 7 | Attention control |
| R cuneus | 4, −88, 16 | Visual |
| R frontal eye field | 27, 11, 54 | Dorsal attention |
| R inferior frontal lobe | 45, −4, 13 | Attention control |
| R inferior parietal lobe | 40, −67, 32 | Default mode |
| R mid frontal gyrus | 39, 11, 38 | Attention control |
| R parahippocampus | 23, −21, −20 | Limbic |
| R posterior intraparietal sulcus | −23, −70, 46 | Dorsal attention |
| R primary auditory cortex | −41, −27, 6 | Auditory |
| R primary visual cortex | 11, −84, 1 | Visual |
| R superior occipital lobe | 15, −79, 23 | Visual |
| R superior temporal junction | 49, −53, 28 | Ventral attention |
| R superior temporal sulcus | 56, −52, 9 | Ventral attention |
| R ventral intraparietal sulcus | 30, −83, 13 | Dorsal attention |

Note:
(ROIs used in the cyclicity analysis are listed alphabetically. L and R designate left and right regions. The center coordinates of the ROI spheres are listed as MNI (x, y, z) coordinates. The primary network membership of the region is presented.)

Cyclicity Analysis

Cyclicity analysis was performed on each time-course to generate a 33×33 skew-symmetric matrix (called the lead matrix), which corresponds to a 528 dimensional vector. A signal is considered cyclic if the values it takes repeat over time. A periodic signal is necessarily cyclic, but a cyclic signal need not be periodic. However, a cyclic signal can be made periodic by an appropriate time re-parameterization. Topological mathematical tools which utilize reparameterization invariant features of paths and path spaces can be used to analyze cyclic signals by simply interpreting signals as paths (Baryshnikov & Schlafly, 2016).

Skew-symmetric matrix: A real matrix A is skew symmetric if $\alpha_{kl} = -\alpha_{lk}$. Such a matrix has eigenvalues that are zero or purely imaginary complex conjugates with corresponding eigenvectors in complex conjugate pairs Periodic signal: A signal or time series is periodic if the shift of time ahead by a value P keeps the series unchanged. The smallest such P is called its period.

Re-parameterization: A re-parameterization of a path over an interval [s, t] is a change of variable $X(t) \to X(\varphi(t))$ such that $X(s) = X(\varphi(s))$, $X(t) = X(\varphi(t))$ and $\varphi(\cdot)$ is continuous, bounded and increasing over [s, t].

Path: An alias for a multidimensional signal, i.e., a d dimensional path is simply a smooth mapping from a subset of the real line to a vector space, e.g., X: [s, t] $\subset$ R $\to$ R$^d$.

To fix notation let R denote the real line and R$^n$ the set of all n-tuples whose elements are real numbers. Let $X_t = X(u)$ be a d-dimensional path in R$^d$ defined over an interval [s, t]. For any such path it is possible to define its n-th iterated integral (see K.-T. Chen, 1958) as, $$X_{s,t}^n = \int_{s<u_1<u_2<\ldots<_t} dX_{u_1} \otimes dX_{u_2} \ldots dX_{u_n}$$

where $\otimes$ denotes the tensor product. Though this short-hand notation for iterated integrals is standard in literature it is important to note that $u_i$ are simply integration variables. For example the first-order iterated integral is simply the increment of the path over [s, t].

$$X_{s,t}^1 = \int_{s<u_1<t} dX_{u_1} = \int_s^t dX(u_1) du_1 = X(t) - X(s)$$

and the second-order iterated integral is:

$$X_{s,t}^2 = \int_{s<u_1<u_2<t} dX_{u_1} \otimes dX_{u_2} = \int_s^t \int_s^{u_2} dX_{u_1} \otimes dX_{u_2}$$

With the definition of the zeroth iterated integral to be 1 the infinite collection of iterated integrals $X^0_{s,t}, X^1_{s,t}, X^2_{s,t}, \ldots$ is called the signature of a path (Chevyrev & Kormilitzin, 2016). The signature of a path defines many of its algebraic and geometric properties, and is invariant under translations as well as re-parameterizations (K.-T. Chen, 1971). Then it is possible to consider the time-course data from each run per subject as a path and construct its truncated signature as an object of interest.

For our purposes, the second-order iterated integral of the closed path (we mean-center and linearly adjust the time course so that it becomes a closed path) gives us meaningful information about the relationships between pairs of ROIs. Each row and column of the constructed lead matrix $$A := \frac{1}{2} \int_{s<u_1<u_2<t} dX_{u_1} \otimes dX_{u_2} - dX_{u_2} \otimes dX_{u_1}$$

can be associated with an ROI, and specifically, each element of the lead matrix corresponds to the signed algebraic area obtained by projecting the n-dimensional path down to a two-coordinate plane (the coordinates being the two ROIs). When this area is positive, the signal in the second ROI (column) can be considered to follow the first ROI (row). Note that the lead matrix for a path X is simply the antisymmetric component of $X^2$. Spectral analysis of the lead matrix then allows for the extraction of other features from the dataset. Specifically we can attribute a strength to the signal from a particular ROI, as well as extract an estimated ordering for the cycle among all the ROIs (Baryshnikov & Schlafly, 2016)

A few simulated and simple cases are shown in FIG. 19. In the case of a path consisting of a single harmonic that is phase shifted, near perfect recovery of the shifts is possible even in the presence of noise, as shown in the first example. The second example demonstrates that with appropriate mean centering and normalization two sets of signals with offsets between them, as well as among the sets themselves can be analyzed to approximately recover the phase offsets. The third example shows how the analysis leads to more involved spectral decomposition of the lead matrix when more than one harmonic is present in the signal. Finally, the last example shows how phase recovery is possible even when the signals themselves are merely cyclic and aperiodic.

Although the first three simulated examples above are trivially solved by Fourier theory, the cyclicity methods extends to cyclic but aperiodic signals. The last example can also be analyzed by methods involving lagged time correlation (Mitra et al., 2015) but the benefit of cyclicity analysis is that the theoretical underpinnings are re-parameterization invariant with respect to time, that is, $X_t \to X\varphi(t)$. This allows one to work under the hypothesis that even though the underlying generative process maybe the same, the time scales involved maybe different.

A preliminary version of the cyclicity analysis toolbox is available online at:
<http://cycapp.herokuapp.com> and more details can be found at:
<http://acnlab.beckman.illinois.edu/#/>.

Stability of Cyclicity Analysis

To assess the stability of a subject's lead matrix across the two sessions, separated by 1 week, we used a k-NN classifier (k=1, cosine metric) to train on the subject's session 1 data and test on session 2 data, and then train on session 2 data and test on session 1 data. Subjects were not separated by group for this analysis. Therefore, each subject could be correctly classified as themselves four times, amongst all of the subjects involved in the study. A high classification rate would mean that the high similarity between the feature space from the subjects lead matrices in one session was sufficient to predict who the subject was in the alternative session.

Classification

Lead matrices were used to classify tinnitus patients from controls following two procedures of dimension reduction. In the first, PCA was used to generate orthogonal components from the lead matrix. The top 10 components were kept for subsequent classification. In the second case, Wilks' lambda values on each of the lead matrix features (ROI pairs) was used to select the most discriminating features for subsequent classification. Classification analyses were performed in Matlab by using the Classification Learner App as well as by using a Classification Toolbox (Ballabio & Consonni, 2013) for the PLS-DA method.

Classification after Dimension Reduction

Dimensionality reduction to 10 dimensions was achieved with PCA to prepare the data for quadratic and linear classification methods. Four methods were chosen for classification: a linear SVM, quadratic SVM, linear DA, and quadratic DA. In addition, 20 component PLS-DA was also implemented as a classification method. PLS regression utilizes the class label information to choose components that best explain the correlation between X and Y (the vector of class labels). In PCA when used as a dimension reduction technique, classification is performed using components generated from the data itself. Therefore, PCA is an excellent method for extracting uncorrelated features in the data, but does not guarantee that these features have discriminatory value in the classification problem. In contrast, in PLS the class information of the training set is used to generate the latent variables that are specifically useful for discrimination. Half of the tinnitus patients and half of the controls were randomly chosen to be part of the training set, and half comprised the test set.

Classification on ROI Pairs Chosen using Wilks' Lambda

The Wilks' lambda criterion can be used to help select the most discriminatory elements in the lead matrix. Lambda values were computed on the whole dataset, but used to inform the selection of variables for the classifier when training on half the dataset and testing on the other half. Since lambda values may be specific to this particular sample, a subset of ROI pairs were further chosen according to which ROI pairs were the most stable across subsets. One thousand Monte Carlo trials were run on half of the dataset to determine which ROI pairs most consistently showed the lowest 20 lambda scores (and therefore had the most stable discriminating power). The top 10 most stable ROI pairs were chosen from this analysis for subsequent classification. The classification rate was based on the average of 100 Monte Carlo trials when training on half of the dataset and testing on the other half.

To provide insights into what functional activity is changing between patients with tinnitus and controls, the 20 ROI pairs with the most discriminating power were further examined. Graphs were made using ROIs corresponding to the most discriminatory features from Wilks' lambda criterion, using the ROIs as nodes and group average value of the feature (from the normalized lead matrix to account for individual differences) as edge weights. To consider the proportion of a group exhibiting a certain directionality one can, instead of normalizing the lead matrix, also set its elements to ±1 depending on direction and observe which relations are flipped at the group level.

REFERENCES

[1] Adjamian, P., Sereda, M., & Hall, D. A. (2009). The mechanisms of tinnitus: Perspectives from human functional neuroimaging. Hearing Research, 253(1-2), 15-31. https://doi.org/10.1016/J.HEARES.2009.04.001

[2] Allan, T. W., Besle, J., Langers, D. R. M., Davies, J., Hall, D. A., Palmer, A. R., & Adjamian, P. (2016). Neuroanatomical alterations in rinnitus assessed with magnetic resonance imaging. Frontiers in Aging Neuroscience, 8, 221. https://doi.org/10.3389/fnagi.2016.00221

[3] Ballabio, D., & Consonni, V. (2013). Classification tools in chemistry. Part 1: Linear models. PLS-DA. Analytical Methods, 5(16), 3790. https://doi.org/10.1039/c3ay40582f

[4] Barkhof, F., Haller, S., & Rombouts, S. A. R. B. (2014). Resting-state functional MR imaging: A new window to the brain. Radiology, 272(1), 29-49. https://doi.org/10.1148/radiol.14132388

[5] Baryshnikov, Y., & Schlafly, E. (2016). Cyclicity in multivariate time series and applications to functional MRI data. In 2016 IEEE 55th conference on decision and control (CDC) (pp. 1625-1630). IEEE. https://doi.org/10.1109/CDC.2016.7798498

[6] Brett, M., Anton, J.-L., Valabregue, R., & Poline, J.-B. (2002). Region of interest analysis using the marsbar toolbox for spm 99. Neuro-Image, 16(2), 5497.

[7] Burton, H., Wineland, A., Bhattacharya, M., Nicklaus, J., Garcia, K. S., & Piccirillo, J. F. (2012). Altered networks in bothersome tinnitus: A functional connectivity study. BMC Neuroscience, 13(1), 3. https://doi.org/10.1186/1471-2202-13-3

[8] Carpenter-Thompson, J. R., Schmidt, S., McAuley, E., & Husain, F. T. (2015). Increased frontal response may underlie decreased tin-nitus severity. PLoS One, 10(12), e0144419. https://doi.org/10. 1371/journal.pone.0144419

[9] Chen, H., Li, K., Zhu, D., Jiang, X., Yuan, Y., Lv, P. Liu, T. (2013). Inferring group-wise consistent multimodal brain networks via multi-view spectral clustering. IEEE Transactions on Medical Imaging, 32(9), 1576-1586. https://doi.org/10.1109/TMI.2013. 2259248

[10] Chen, K.-T. (1958). Integration of paths—A faithful representation of paths by non-commutative formal power series. Transactions of the American Mathematical Society, 89(2), 395-395. https://doi.org/10.1090/S0002-9947-1958-0106258-0

[11] Chen, K.-T. (1971). Algebras of iterated path integrals and fundamental groups. Transactions of the American Mathematical Society, 156, 359-359. https://doi.org/10.1090/S0002-9947-1971-0275312-1

[12] Chevyrev, I., & Kormilitzin, A. (2016). A primer on the signature method in machine learning. arXiv, [stat.ML], 45. Retrieved from http://arxiv.org/abs/1603.03788

[13] Davies, J. E., Gander, P. E., & Hall, D. A. (2017). Does chronic tinnitus alter the emotional response function of the amygdala?: A sound-evoked fMRI study. Frontiers in Aging Neuroscience, 9(February). https://doi.org/10.3389/fnagi.2017.00031

[14] Fox, M. D., Snyder, A. Z., Vincent, J. L., Corbetta, M., Van Essen, D. C., & Raichle, M. E. (2005). The human brain is intrinsically organized into dynamic, anticorrelated functional networks. Proceedings of the National Academy of Sciences of the United States of America, 102(27), 9673-8. https://doi.org/10. 1073/pnas.0504136102

[15] Friston, K. J., Holmes, A. P., & Worsley, K. J. (1999). How many subjects constitute a study? NeuroImage, 10(1), 1-5. https://doi.org/10.1006/NIMG.1999.0439

[16] Husain, F. T. (2016). Neural networks of tinnitus in humans: Elucidating severity and habituation. Hearing Research, 334, 37-48. https://doi.org/10.1016/J.HEARES.2015.09.010

[17] Husain, F. T., & Schmidt, S. A. (2014). Using resting state functional connectivity to unravel networks of tinnitus. Hearing Research, 307, 153-162. https://doi.org/10.1016/J.HEARES.2013.07.010

[18] Keilholz, S. D. (2014). The neural basis of time-varying resting-state functional connectivity. Brain Connectivity, 4(10), 769-779. https://doi.org/10.1089/brain.2014.0250

[19] Mannfolk, P., Nilsson, M., Hansson, H., Stahlberg, F., Fransson, P., Weibull, A., . . . Olsrud, J. (2011). Can resting-state functional MRI serve as a complement to task-based mapping of sensori-motor function? A test-retest reliability study in healthy volunteers. Journal of Magnetic Resonance Imaging, 34(3), 511-517. https://doi.org/10.1002/jmri.22654

[20] Mantini, D., Perrucci, M. G., Del Gratta, C., Romani, G. L., & Corbetta, M. (2007). Electrophysiological signatures of resting state networks in the human brain. Proceedings of the National Academy of Sciences of the United States of America, 104(32), 13170-5. https://doi.org/10.1073/pnas.0700668104

[21] Maudoux, A., Lefebvre, P., Cabay, J.-E., Demertzi, A., Vanhaudenhuyse, A., Laureys, S., & Soddu, A. (2012a). Auditory resting-state network connectivity in tinnitus: A functional MM study. PLoS One, 7(5), e36222. https://doi.org/10.1371/journal.pone.0036222

[22] Maudoux, A., Lefebvre, P., Cabay, J. E., Demertzi, A., Vanhaudenhuyse, A., Laureys, S., & Soddu, A. (2012b). Connectivity graph analysis of the auditory resting state network in tinnitus. Brain Research, 1485, 10-21. https://doi.org/10.1016/J.BRAINRES.2012.05.006

[23] Mitra, A., Snyder, A. Z., Blazey, T., & Raichle, M. E. (2015). Lag threads organize the brain's intrinsic activity. Proceedings of the National Academy of Sciences of the United States of America, 112(17), E2235-44. https://doi.org/10.1073/pnas. 1503960112

[24] Møller, A. R. (2007). Tinnitus: Presence and future. Progress in Brain Research, 166, 3-16. https://doi.org/10.1016/S0079-6123(07)66001-4

[25] Raichle, M. E., & Snyder, A. Z. (2007). A default mode of brain function: A brief history of an evolving idea. NeuroImage, 37(4), 1083-1090. https://doi.org/10.1016/J.NEUROIMAGE.2007.02.041

[26] Schmidt, S. A., Akrofi, K., Carpenter-Thompson, J. R., & Husain, F. T. (2013). Default mode, dorsal attention and auditory resting state networks exhibit differential functional connectivity in tinnitus and hearing loss. PLoS One, 8(10), e76488. https://doi.org/10.1371/journal.pone.0076488

[27] Schmidt, S. A., Carpenter-Thompson, J., & Husain, F. T. (2017). Connectivity of precuneus to the default mode and dorsal attention network: A possible invariant marker of long-term tinnitus. NeuroImage: Clinical, 16, 196-204. https://doi.org/10.1016/J.NICL.2017.07.015

[28] Shehzad, Z., Kelly, A. M. C., Reiss, P. T., Gee, D. G., Gotimer, K., Uddin, L. Q., . . . Milham, M. P. (2009). The resting brain: Unconstrained yet reliable. Cerebral Cortex, 19(10), 2209-2229. https://doi.org/10.1093/cercor/bhn256

[29] Sheline, Y. I., Barch, D. M., Donnelly, J. M., Ollinger, J. M., Snyder, A. Z., & Mintun, M. A. (2001). Increased amygdala response to masked emotional faces in depressed subjects resolves with anti-depressant treatment: An fMRI study. Biological Psychiatry, 50(9), 651-658. https://doi.org/10.1016/50006-3223(01)01263-X

[30] Shulman, G. L., Fiez, J. A., Corbetta, M., Buckner, R. L., Miezin, F. M., Raichle, M. E., & Petersen, S. E. (1997). Common blood flow changes across visual tasks: II. Decreases in cerebral cortex. Journal of Cognitive Neuroscience, 9(5), 648-663. https://doi.org/10.1162/jocn.1997.9.5.648

[31] Simonetti, P., & Oiticica, J. (2015). Tinnitus neural mechanisms and structural changes in the brain: The contribution of neuroimaging research. International Archives of Otorhinolaryngology, 19(03), 259-265. https://doi.org/10.1055/s-0035-1548671

[32] Trevis, K. J., McLachlan, N. M., & Wilson, S. J. (2016). Cognitive mechanisms in chronic tinnitus: Psychological markers of a failure to switch attention. Frontiers in Psychology, 7, 1262. https://doi.org/10.3389/fpsyg.2016.01262

[33] Veer, I. M., Beckmann, C., Van Tol, M.-J., Ferrarini, L., Milles, J., Veltman, D. Rombouts, S. A. R. (2010). Whole brain resting-state analysis reveals decreased functional connectivity in major depression. Frontiers in Systems Neuroscience, 4, 41. https://doi. org/10.3389/fnsys.2010.00041

[34] Wineland, A. M., Burton, H., & Piccirillo, J. (2012). Functional connectivity networks in nonbothersome tinnitus. Otolaryngology-Head and Neck Surgery, 147(5), 900-906. https://doi.org/10. 1177/0194599812451414

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

STATEMENTS REGARDING INCORPORATION BY REFERENCE AND VARIATIONS

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, exemplary embodiments and optional features, modification and variation of the concepts herein disclosed may be resorted to by those skilled in the art, and that such modifications and variations are considered to be within the scope of this invention as defined by the appended claims. The specific embodiments provided herein are examples of useful embodiments of the present invention and it will be apparent to one skilled in the art that the present invention may be carried out using a large number of variations of the devices, device components, methods steps set forth in the present description. As will be obvious to one of skill in the art, methods and devices useful for the present methods can include a large number of optional composition and processing elements and steps.

When a group of substituents is disclosed herein, it is understood that all individual members of that group and all subgroups of the group members, are disclosed separately. When a Markush group or other grouping is used herein, all individual members of the group and all combinations and subcombinations possible of the group are intended to be individually included in the disclosure.

Every formulation or combination of components described or exemplified herein can be used to practice the invention, unless otherwise stated.

Whenever a range is given in the specification, for example, a temperature range, a time range, or a composition or concentration range, all intermediate ranges and subranges, as well as all individual values included in the ranges given are intended to be included in the disclosure. It will be understood that any subranges or individual values in a range or subrange that are included in the description herein can be excluded from the claims herein.

All patents and publications mentioned in the specification are indicative of the levels of skill of those skilled in the art to which the invention pertains. References cited herein are incorporated by reference herein in their entirety to indicate the state of the art as of their publication or filing date and it is intended that this information can be employed herein, if needed, to exclude specific embodiments that are in the prior art. For example, when composition of matter are claimed, it should be understood that compounds known and available in the art prior to Applicant's invention, including compounds for which an enabling disclosure is provided in the references cited herein, are not intended to be included in the composition of matter claims herein.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms. The invention illustratively described herein suitably may be practiced in the absence of any element or elements, limitation or limitations which is not specifically disclosed herein.

One of ordinary skill in the art will appreciate that starting materials, biological materials, reagents, synthetic methods, purification methods, analytical methods, assay methods, and biological methods other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

We claim:

1. A method for determining a tinnitus condition of a patient comprising:
   providing a functional magnetic resonance imaging (fMRI) device;
   imaging said patient with said fMRI device thereby generating a fMRI map of at least a portion of a brain of said patient;
   identifying a plurality of voxels in said fMRI map corresponding to regions of the at least a portion of said brain of said patient;
   analyzing said plurality of voxels, thereby determining the tinnitus condition of said patient;
   wherein the analyzing step comprises identifying a functional connection between voxels corresponding to a first region of said brain and voxels corresponding to a second region of said brain; and
   wherein the first region is an amygdala region and the second region is a precuneus region of said brain of said patient.

2. The method of claim 1, wherein said imaging step is performed in a resting state of said patient.

3. The method of claim 1, wherein said tinnitus condition is the presence of or absence of tinnitus in said patient.

4. The method of claim 1, wherein said tinnitus condition is a stage of progression of tinnitus in said patient.

5. The method of claim 1, wherein said tinnitus condition is a type or severity of tinnitus of said patient.

6. The method of claim 1, wherein said patient is currently undergoing a treatment for tinnitus and said tinnitus condition is a measure of efficacy of said treatment.

7. The method of claim 1, wherein said step of identifying a plurality of voxels identifies a number of voxels selected from the range of 10 to 40 voxels.

8. The method of claim 1, wherein said step of identifying a plurality of voxels identifies a number of voxels greater than or equal to 15 voxels.

9. The method of claim 1, wherein said imaging step is performed over a predetermined period of time and wherein each of said plurality of voxels includes a time component.

10. The method of claim 9, wherein said step of analyzing said plurality of voxels includes analyzing said plurality of voxels in the time domain.

11. The method of claim 9, wherein said step of analyzing said plurality of voxels further comprises invariant analysis with respect to parametrization of activity in said voxels with respect to time.

12. The method of claim 1, wherein said imaging step generates said fMRI map as a time series of blood oxygen levels corresponding to a time period of greater than or equal to 5 minutes.

13. The method of claim 12, wherein said step of analyzing said plurality of voxels analyzes each voxel over a time interval of less than or equal to 10 seconds.

14. A method for determining a tinnitus condition of a patient comprising:
    providing a functional magnetic resonance imaging (fMRI) device;
    imaging said patient with said fMRI device thereby generating a fMRI map of at least a portion of a brain of said patient;
    identifying a plurality of voxels in said fMRI map corresponding to regions of the at least a portion of said brain of said patient;
    analyzing said plurality of voxels, thereby determining the tinnitus condition of said patient, wherein the analyzing step comprises:
       iteratively integrating at least a portion of a time series corresponding to each of said plurality of voxels thereby generating a plurality of irreducible trajectories;
       generating a lead matrix comprised of a plurality of signed areas wherein determination of sign is informed by the direction of traversal of said irreducible trajectories; and
       identifying a functional connection between voxels corresponding to a first region of said brain and voxels corresponding to a second region of said brain.

15. The method of claim 14, wherein said step of analyzing said plurality of voxels utilizes a chain of offsets model.

16. The method of claim 1, wherein said step of analyzing said plurality of voxels further comprises a step of reducing noise in said fMRI map.

17. The method of claim 1, wherein said step of analyzing said plurality of voxels further comprises comparing said plurality of voxels to a library of voxel data in order to determine said tinnitus condition.

18. The method of claim 1, wherein said step of analyzing said plurality of voxels further comprises comparing said one or more functional connections to a library of connection data in order to determine said tinnitus condition.

19. The method of claim 18, wherein said comparing step is performed by a processor utilizing machine learning.

20. The method of claim 1, wherein said fMRI map corresponds to a portion of said brain of said patient.

21. The method of claim 1, wherein said fMRI map corresponds to substantially all of said brain of said patient.

22. The method of claim 1, wherein said fMRI map is a three dimensional representation of said patient's brain over time.

23. The method of claim 1, wherein the analyzing step comprises identifying an additional functional connection between voxels corresponding to a third region of said brain and voxels corresponding to a fourth region of said brain.

* * * * *